United States Patent
Soper et al.

(10) Patent No.: US 12,303,209 B2
(45) Date of Patent: May 20, 2025

(54) SYSTEMS FOR EVALUATING REGISTERABILITY OF ANATOMIC MODELS AND ASSOCIATED METHODS

(71) Applicant: INTUITIVE SURGICAL OPERATIONS, INC., Sunnyvale, CA (US)

(72) Inventors: Timothy D. Soper, San Jose, CA (US); Tao Zhao, Sunnyvale, CA (US); Federico Barbagli, San Francisco, CA (US); Pechin Chien Pau Lo, Santa Clara, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 343 days.

(21) Appl. No.: 18/002,840

(22) PCT Filed: May 11, 2021

(86) PCT No.: PCT/US2021/031835
§ 371 (c)(1),
(2) Date: Dec. 21, 2022

(87) PCT Pub. No.: WO2022/005621
PCT Pub. Date: Jan. 6, 2022

(65) Prior Publication Data
US 2023/0240750 A1    Aug. 3, 2023

Related U.S. Application Data

(60) Provisional application No. 63/046,584, filed on Jun. 30, 2020.

(51) Int. Cl.
*A61B 34/10*   (2016.01)
*A61B 1/00*    (2006.01)
*G06T 19/20*   (2011.01)

(52) U.S. Cl.
CPC ........ *A61B 34/10* (2016.02); *A61B 1/000094* (2022.02); *G06T 19/20* (2013.01); *A61B 2034/105* (2016.02); *G06T 2219/2004* (2013.01)

(58) Field of Classification Search
None
See application file for complete search history.

(56) References Cited

U.S. PATENT DOCUMENTS

| | | | |
|---|---|---|---|
| 6,389,187 B1 | 5/2002 | Greenaway et al. | |
| 7,772,541 B2 | 8/2010 | Froggatt et al. | |

(Continued)

FOREIGN PATENT DOCUMENTS

| | | |
|---|---|---|
| WO | WO-2017030915 A1 | 2/2017 |
| WO | WO-2017185170 A1 | 11/2017 |

(Continued)

OTHER PUBLICATIONS

International Preliminary Report on Patentability for Application No. PCT/US2021/031835 mailed Jan. 12, 2023, 12 pages.

(Continued)

*Primary Examiner* — Anh-Tuan V Nguyen
(74) *Attorney, Agent, or Firm* — Haynes & Boone, LLP.

(57) ABSTRACT

Devices, systems, methods, and computer program products for planning medical procedures are disclosed herein. In some embodiments, a system for planning a medical procedure includes a processor and memory operably coupled to the processor. The memory stores instructions that, when executed by the processor, cause the system to perform operations including receiving a three-dimensional model of an anatomic region of a patient and evaluating whether the three-dimensional model is suitable for use in a registration procedure to be performed in the anatomic region. The evaluating includes: analyzing a span of the three-dimen- (Continued)

sional model along at least two different directions, determining whether the three-dimensional model includes at least one segmented component corresponding to at least one structure of the anatomic region, and performing a registration between the three-dimensional model and a virtual registration data set.

20 Claims, 11 Drawing Sheets

(56) References Cited

U.S. PATENT DOCUMENTS

| | | | |
|---|---|---|---|
| 7,781,724 B2 | 8/2010 | Childers et al. | |
| 2006/0013523 A1 | 1/2006 | Childlers et al. | |
| 2016/0155236 A1* | 6/2016 | Davey | G06T 15/08 |
| | | | 382/131 |
| 2018/0153621 A1* | 6/2018 | Duindam | A61B 34/35 |
| 2022/0071715 A1 | 3/2022 | Donhowe et al. | |
| 2022/0265357 A1* | 8/2022 | Morvan | A61B 90/361 |
| 2022/0343504 A1 | 10/2022 | Donhowe et al. | |

FOREIGN PATENT DOCUMENTS

| | | |
|---|---|---|
| WO | WO-2019217366 A1 | 11/2019 |
| WO | WO-2020056086 A1 | 3/2020 |

OTHER PUBLICATIONS

International Search Report and Written Opinion for Application No. PCT/US2021/031835, mailed Oct. 27, 2021, 17 pages.
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

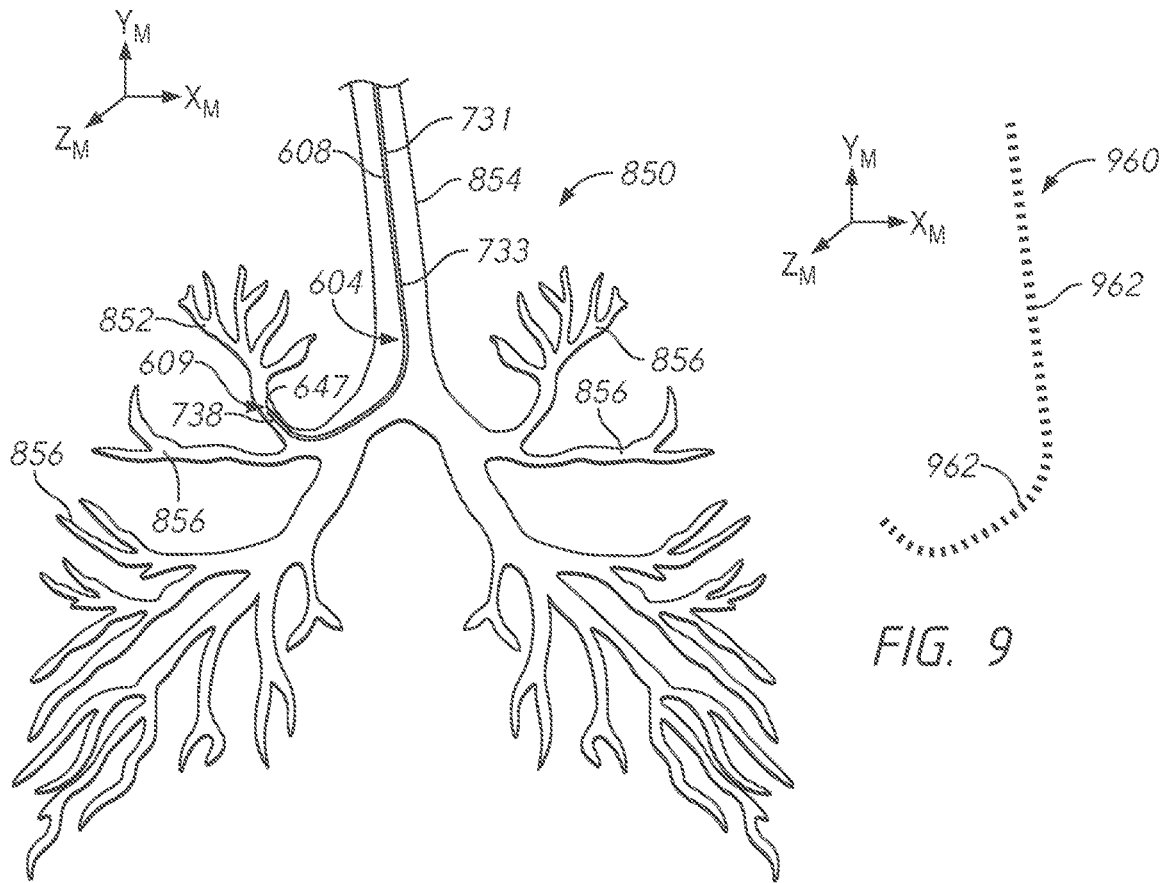
FIG. 8
FIG. 9
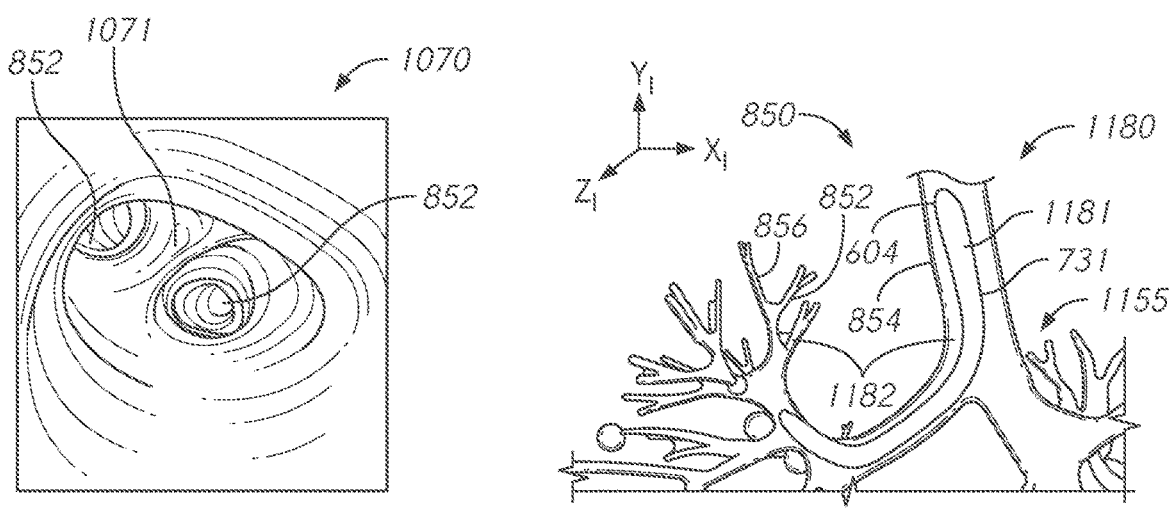
FIG. 10
FIG. 11

SYSTEMS FOR EVALUATING REGISTERABILITY OF ANATOMIC MODELS AND ASSOCIATED METHODS

CROSS-REFERENCE TO RELATED APPLICATION(S)

The present application is the U.S. National Stage patent application of International Patent Application No. PCT/US2021/031835, filed May 11, 2021 which claims the benefit of U.S. Provisional Application No. 63/046,584, filed Jun. 30, 2020, all of which are incorporated herein by reference in their entirety.

TECHNICAL FIELD

The present disclosure is directed to systems, methods, and computer program products for evaluating registerability of a model of an anatomic region and other aspects of planning a registration procedure.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions, an operator may insert minimally invasive medical tools to reach a target tissue location. Minimally invasive medical tools include instruments such as therapeutic, diagnostic, biopsy, and surgical instruments. Medical tools may be inserted into anatomic passageways and navigated toward a region of interest within a patient anatomy. Navigation may be assisted using images of the anatomic passageways. Improved systems and methods are needed to accurately perform registrations between medical tools and images of the anatomic passageways.

SUMMARY

Disclosed herein are devices, systems, methods, and computer program products for planning medical procedures, including evaluating whether a model of an anatomic region is suitable for use in a registration procedure and/or determining a survey trajectory to be navigated by a medical device during the registration procedure. In some embodiments, a system for planning a medical procedure includes a processor and memory operably coupled to the processor. The memory can store instructions that, when executed by the processor, cause the system to perform operations including receiving a three-dimensional model of an anatomic region of a patient and evaluating whether the three-dimensional model is suitable for use in a registration procedure to be performed in the anatomic region. The evaluating can include: analyzing a span of the three-dimensional model along at least two different directions, determining whether the three-dimensional model includes at least one segmented component corresponding to at least one structure of the anatomic region, and performing a registration between the three-dimensional model and a virtual registration data set.

In these and other embodiments, a non-transitory, computer-readable medium can store instructions that, when executed by one or more processors of a computing system, cause the computing system to perform operations including receiving a three-dimensional model of an anatomic region of a patient and evaluating whether the three-dimensional model is suitable for use in a registration procedure to be performed in the anatomic region. The evaluating can include: analyzing a span of the three-dimensional model along at least two different directions, determining whether the three-dimensional model includes at least one segmented component corresponding to at least one structure of the anatomic region, and performing a registration between the three-dimensional model and a virtual registration data set.

In these and still other embodiments, a method can include receiving a three-dimensional model of an anatomic region of a patient and evaluating whether the three-dimensional model is suitable for use in a registration procedure to be performed in the anatomic region. The evaluating can include: analyzing a span of the three-dimensional model along at least two different directions, determining whether the three-dimensional model includes at least one segmented component corresponding to at least one structure of the anatomic region, and performing a registration between the three-dimensional model and a virtual registration data set.

In these and further embodiments, a system for planning a medical procedure includes a processor and memory operably coupled to the processor. The memory can store instructions that, when executed by the processor, cause the system to perform operations including: receiving a three-dimensional model of an anatomic region of a patient; generating a survey trajectory through a portion of the three-dimensional model; generating a virtual registration data set including a plurality of data points along or near the survey trajectory; performing a plurality of registrations between the three-dimensional model and the virtual registration data set; and evaluating, based on the plurality of registrations, whether the survey trajectory is suitable for use in a registration procedure to be performed in the anatomic region.

In these and other embodiments, a non-transitory, computer-readable medium can store instructions that, when executed by one or more processors of a computing system, cause the computing system to perform operations including: receiving a three-dimensional model of an anatomic region of a patient; generating a survey trajectory through a portion of the three-dimensional model; generating a virtual registration data set including a plurality of data points along or near the survey trajectory; performing a plurality of registrations between the three-dimensional model and the virtual registration data set; and evaluating, based on the plurality of registrations, whether the survey trajectory is suitable for use in a registration procedure to be performed in the anatomic region.

In these and still other embodiments, a method can include: receiving a three-dimensional model of an anatomic region of a patient; generating a survey trajectory through a portion of the three-dimensional model; generating a virtual registration data set including a plurality of data points along or near the survey trajectory; performing a plurality of registrations between the three-dimensional model and the virtual registration data set; and evaluating, based on the plurality of registrations, whether the survey trajectory is suitable for use in a registration procedure to be performed in the anatomic region.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure. The drawings should not be taken to limit the disclosure to the specific embodiments depicted, but are for explanation and understanding only.

FIG. 8 is a schematic representation of a portion of the medical instrument system of FIG. 7 extended within an anatomic region of a patient in accordance with various embodiments of the present technology.

FIG. 9 illustrates a plurality of coordinate points forming a point cloud representing a shape of the portion of the medical instrument system of FIG. 8 configured in accordance with various embodiments of the present technology.

FIG. 10 illustrates a real navigational image of real patient anatomy from a viewpoint of the portion of the medical instrument system of FIG. 8 extended within the anatomic region of FIG. 8 in accordance with various embodiments of the present technology.

FIG. 11 illustrates an intraoperative image of a portion of the anatomic region of FIG. 8 while the portion of the medical instrument system of FIG. 8 is extended within the anatomic region in accordance with various embodiments of the present technology.

DETAILED DESCRIPTION

Figure 1:
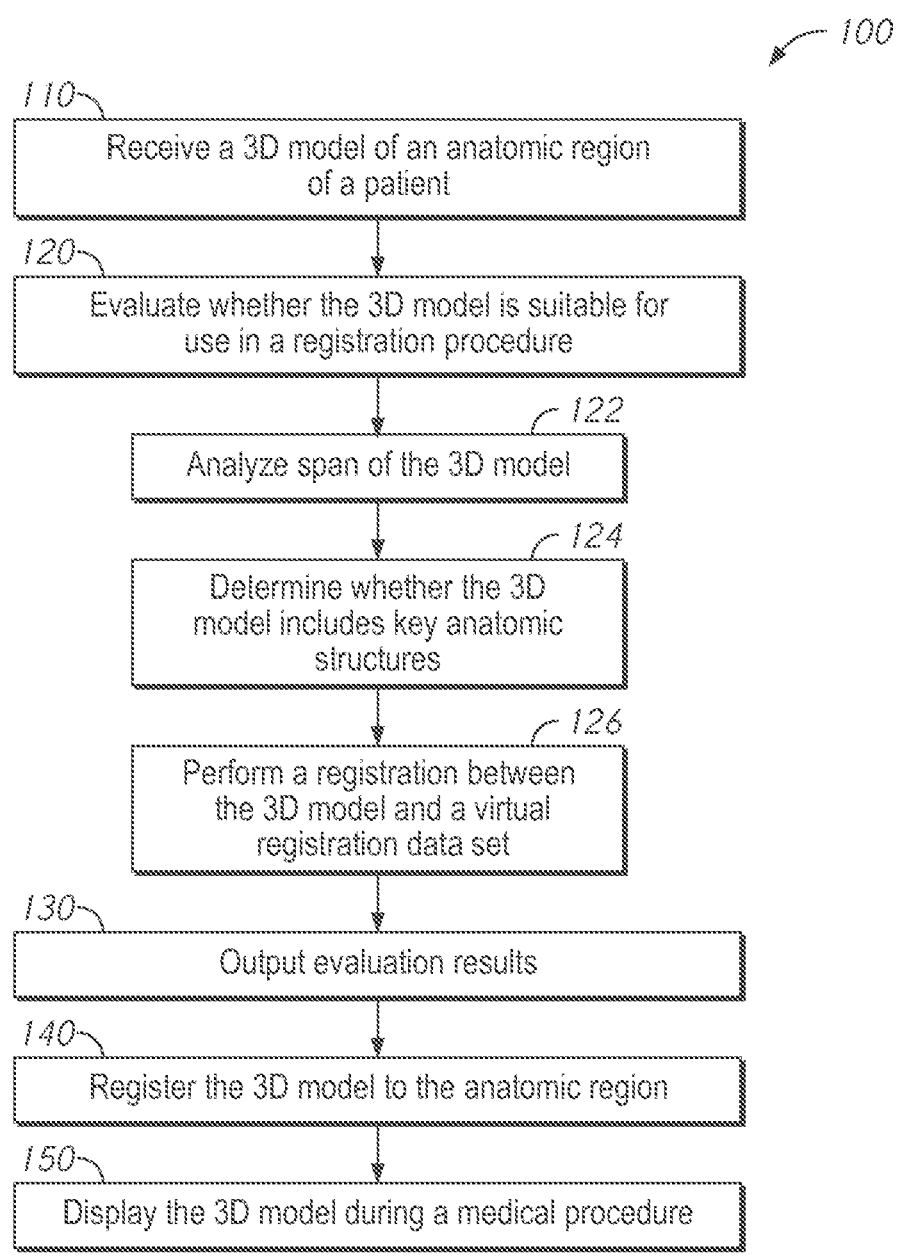
FIG. 1 is a flow diagram illustrating a method for evaluating registerability of a model of an anatomic region in accordance with various embodiments of the present technology.

The present disclosure is directed to devices, systems, methods, and computer program products for planning a medical procedure to be performed within an anatomic region of a patient. In some embodiments, an image-guided medical procedure uses a three-dimensional model of the anatomic region to assist an operator in navigating a medical device or instrument within the patient. The three-dimensional model is registered to the patient anatomy so that the position of the device within the patient can be tracked and mapped to a corresponding position within the model. Accurate registration may be particularly important for medical procedures performed within complex, dense, and/or tortuous anatomic regions, such as the airways of the lungs. However, if the three-dimensional model cannot be accurately registered to the anatomy (e.g., due to insufficient model data, complexity of the anatomic region, etc.), it may be difficult or impossible for the operator to navigate the medical device to the correct locations within the anatomic region.

Accordingly, in some embodiments, the systems described herein are configured to evaluate the anatomic model during preoperative planning to determine whether the model is suitable for registration to the anatomic region (i.e., can be accurately and consistently registered to at least a portion of the patient's anatomy). The evaluation can include, for example, analyzing whether the model has sufficient span along at least two different directions and/or determining whether the model includes key anatomic structures (e.g., trachea, main carina, left main bronchus, right main bronchus, and/or sub-segmental bronchus). In some embodiments, the evaluating includes performing one or more registrations between the three-dimensional model and one or more virtual registration data sets. The results of these simulated registrations can be used to assess whether the model is suitable for use in the actual registration procedure, or whether the model should be revised. By providing feedback on the model during the preoperative planning phase, the present technology is expected to reduce the likelihood of delays, cancellations, or other setbacks due to inaccurate registration during the actual medical procedure.

Additionally, during the registration procedure, it may be challenging to determine how to survey the anatomic region with the medical device to obtain sufficient data to accurately register the model to the anatomic region. Thus, in some embodiments, the systems disclosed herein aid in planning the registration procedure by determining which survey trajectory or trajectories are likely to produce an accurate registration. For example, the systems disclosed herein can generate a proposed survey trajectory through at least a portion of the three-dimensional model, and then generate a virtual registration data set that simulates survey data obtained by a medical device following the survey trajectory. The systems disclosed herein can then perform a plurality of registrations between the three-dimensional model and the virtual registration data set to evaluate whether the survey trajectory is likely to produce a successful registration. If the survey trajectory is determined to be suitable, it can be displayed to the operator for visual guidance during the actual registration procedure. As a result, the present technology is expected to improve the efficiency and accuracy of the registration procedure.

A. EMBODIMENTS OF TECHNIQUES FOR EVALUATING REGISTERABILITY OF ANATOMIC MODELS AND PLANNING REGISTRATION PROCEDURES

The present technology is directed to preoperative planning for a medical procedure to be performed in an anatomic region of a patient. In some embodiments, for example, the systems described herein are configured to evaluate the registerability of a three-dimensional model of the anatomic region—i.e., whether the model is suitable for use in a subsequent registration procedure. The registration procedure can involve determining a transformation that maps the reference frame of the model to the reference frame of the patient anatomy. As discussed above, an accurate registration allows the position of a medical device to be mapped to a corresponding position in the three-dimensional model so the operator can refer to the model for visual guidance in navigating the device to a target location in the patient anatomy. The accuracy of the registration may be compromised, however, if the model does not include enough data of the anatomic region (e.g., lacks sufficient span along multiple directions, lacks certain anatomic structures), if the fit of the model to the anatomic region is ambiguous (e.g., due to high density of passageways within the anatomic region), or if the model is otherwise unable to support a stable and consistent registration. These issues can be mitigated by evaluating the registerability of the model during the preoperative planning phase, thus allowing the model to be revised if needed before the actual registration procedure is performed in the patient.

FIG. 1 is a flow diagram illustrating a method 100 for evaluating registerability of a model of an anatomic region in accordance with various embodiments of the present technology. The method 100 is illustrated as a set of steps or processes 110-150. All or a subset of the steps of the method 100 can by implemented by a computing system or device, such as a workstation, including a portable computing system, such as a laptop computer, configured to perform preoperative planning for a medical procedure. Alternatively, all or a subset of the steps of the method 100 can be implemented by a control system of a medical instrument system or device, including various components or devices of a robotic or teleoperated system. The computing system for implementing the method 100 can include one or more processors operably coupled to a memory storing instructions that, when executed, cause the computing system to perform operations in accordance with the steps 110-150. The method 100 is illustrated in the following by cross-referencing various aspects of FIGS. 2A, 2B, 2C, 3, and 4.

The method 100 begins at step 110 with receiving a three-dimensional model of an anatomic region of a patient. The model can represent an anatomic region in which a medical procedure is to be performed (e.g., the airways of the patient's lungs), and can represent the locations, shapes, and connectivity of the passageways and other structures within that region. In some embodiments, the three-dimensional model is generated from preoperative image data of the anatomic region, such as computed tomography (CT) data, magnetic resonance imaging (MRI) data, fluoroscopy data, thermography data, ultrasound data, optical coherence tomography (OCT) data, thermal image data, impedance data, laser image data, nanotube X-ray image data, and/or other suitable data representing the patient anatomy. The image data can correspond to two-dimensional, three-dimensional, or four-dimensional (e.g., time-based or velocity-based information) images. In some embodiments, for example, the image data includes two-dimensional images from multiple perspectives that can be combined into pseudo-three-dimensional images.

The three-dimensional model can be generated by segmenting graphical elements in the image data that represent anatomic features. During the segmentation process, pixels or voxels generated from the image data may be partitioned into segments or elements and/or be tagged to indicate that they share certain characteristics or computed properties such as color, density, intensity, and texture. The segments or elements associated with anatomical features of the patient are then converted into a segmented anatomic model, which is generated in a model or image reference frame. To represent the model, the segmentation process may delineate sets of voxels representing the anatomic region and then apply a function, such as marching cube function, to generate a three-dimensional surface that encloses the voxels. The model may be made by generating a mesh, volume, or voxel map. Additionally or alternatively, the model may include a centerline model that includes a set of interconnected line segments or points extending through the centers of the modeled passageways. Where the model includes a centerline model including a set of interconnected line segments, those line segments may be converted to a cloud or set of points. By converting the line segments, a desired quantity of points corresponding to the interconnected line segments can be selected manually or automatically.

At step 120, the three-dimensional model is evaluated to determine whether it is suitable for use in a subsequent registration procedure. As discussed above, the model may be considered suitable if it is likely to produce an accurate registration to the patient's anatomy, or at least a portion thereof. The evaluation procedure can involve analyzing various aspects of the model to assess its registerability. In some embodiments, the evaluation procedure is used to assess the registerability of the entire model. In other embodiments, however, the evaluation procedure can be used to assess the registerability of one or more selected portions of the model. For example, registerability can be assessed only for portions of the model corresponding to anatomic locations where accurate registration is expected to be particularly important, such as locations at or near a site of interest for the subsequent medical procedure (e.g., a target lesion to be biopsied).

At step 122, for example, the span of the three-dimensional model is analyzed. The span of the model can correspond to the extent of the anatomic region covered by the model. The model can be considered unsuitable for registration if it does not have sufficient span—i.e., the model does not cover enough of the anatomic region to allow for accurate registration to that region. As discussed above, the span may be evaluated over the entire model, or over a specific anatomic sub-region (e.g., a lobe) where a site of interest (e.g., a lesion) may reside and/or where accurate registration is most critical.

In some embodiments, for example, the analysis includes determining whether the model has sufficient span along at least two different dimensions or directions (e.g., a superior-inferior direction and a medial-lateral direction). A model that includes sufficient span only along a first direction (e.g., a superior-inferior direction) and lacks sufficient span along a second direction (e.g., a medial-lateral direction) may be considered inadequate for registration, while a model that includes sufficient span along two or more different directions may be considered suitable for registration. In some embodiments, the two or more different directions correspond to known cardinal directions (e.g., a superior-inferior direction, a medial-lateral direction, etc.). In other embodiments, however, the two or more different directions can be randomized directions, e.g., to ensure the model provides sufficient coverage in a three-dimensional space.

Figure 2A:
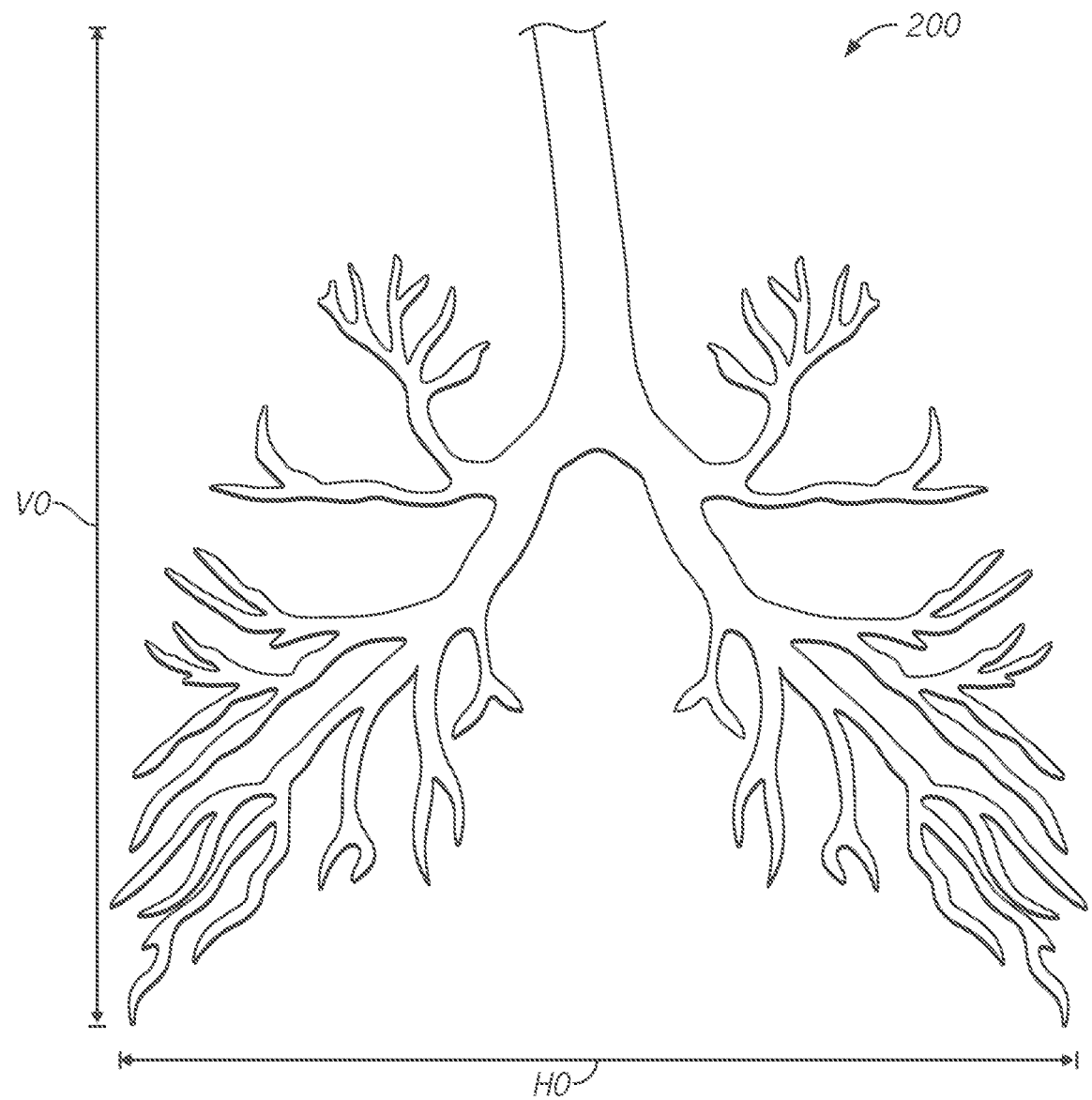
FIG. 2A is a schematic illustration of the airways of the lungs.
Figure 2B:
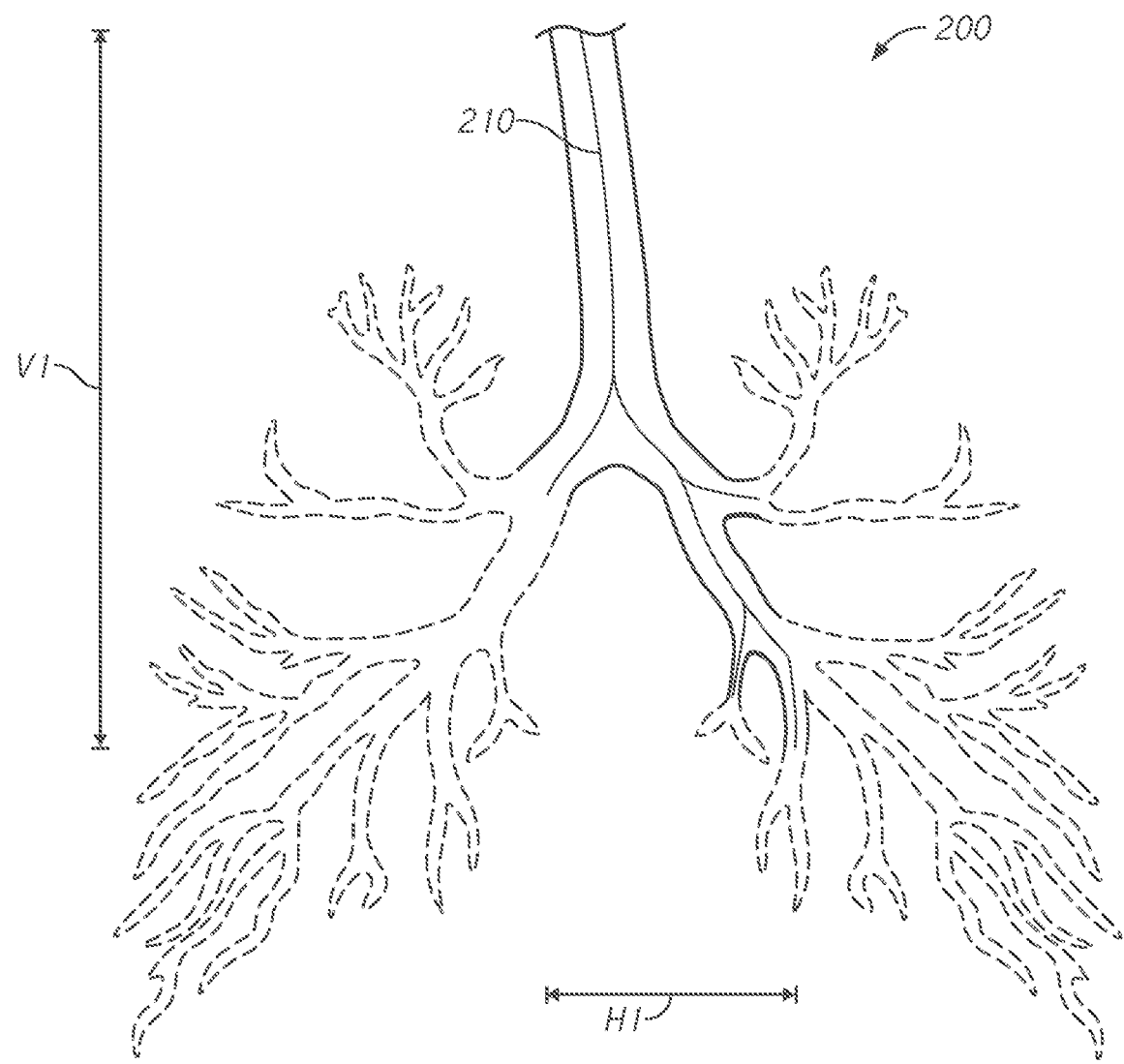
FIG. 2B is a schematic illustration of a model of the airways of FIG. 2A that has insufficient horizontal span.
Figure 2C:
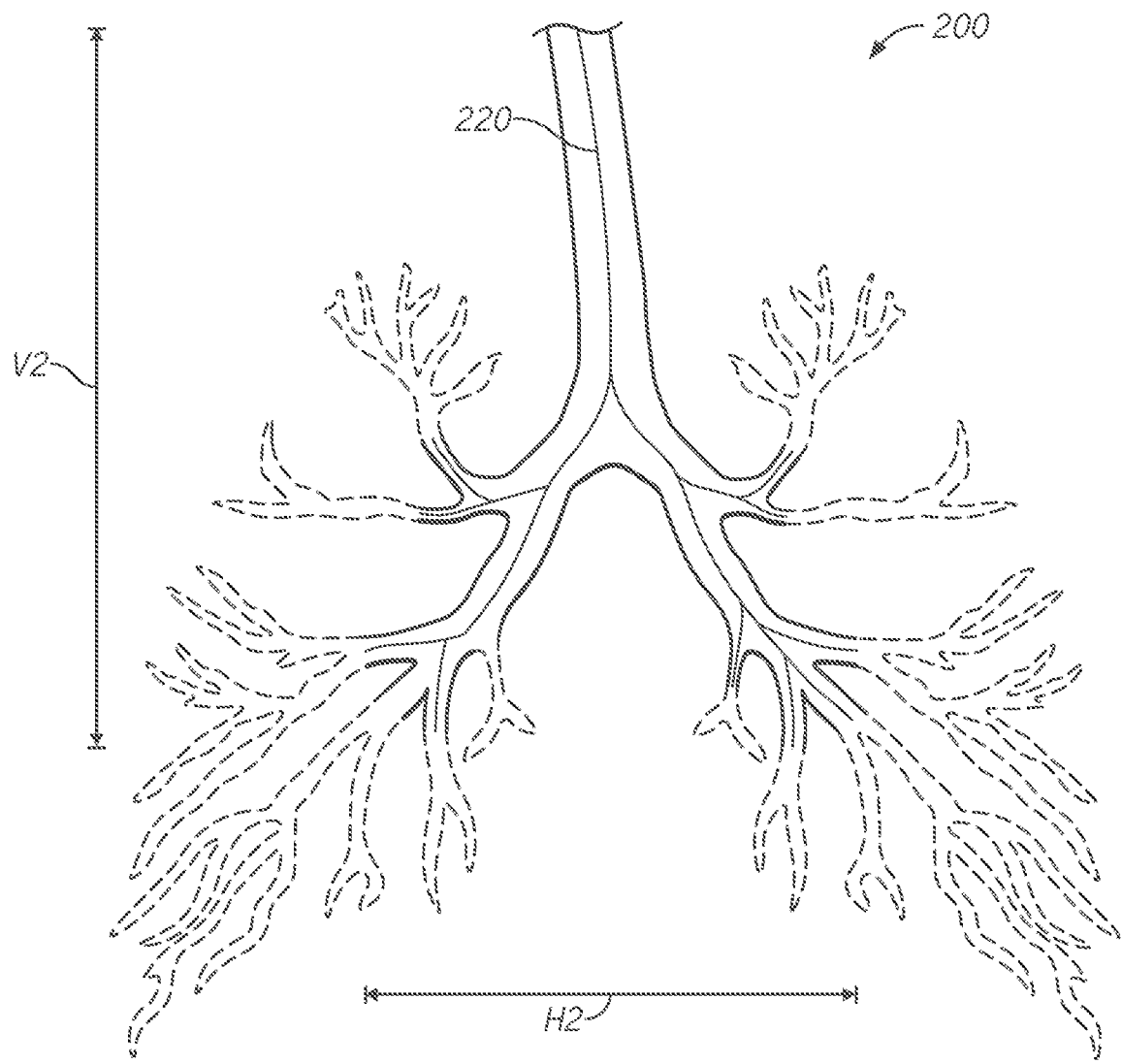
FIG. 2C is a schematic illustration of a model of the airways of FIG. 2A that has sufficient horizontal span.

FIGS. 2A-2C are schematic illustrations of the concept of span with respect to airways 200 of a patient's lungs. Referring first to FIG. 2A, the airways 200 include a plurality of branches or bifurcations that extend along at least two different directions, such as a vertical (superior-inferior) direction $V_0$ and a horizontal (medial-lateral) direction $H_0$. The span of a model of the airways 200 can correspond to the amount of branches/bifurcations represented in the model. Referring to FIG. 2B, for example, the model 210 does not cover enough branches/bifurcations of the airways 200 (as indicated by the broken lines in FIG. 2B), such that the model 210 has sufficient vertical span $V_1$ but insufficient horizontal span $H_1$. As a result, the model 210 is likely to produce a poor registration to the airways 200. Referring next to FIG. 2C, the model 220 covers enough branches/bifurcations of the airways 200 such that the model 220 has sufficient vertical span $V_2$ and sufficient horizontal span $H_2$. Accordingly, the model 220 is likely to produce an accurate registration to the airways 200.

In some embodiments, the span of the three-dimensional model is analyzed by a calculating a first span value along a first direction and a second span value along a second direction different from (e.g., orthogonal to) the first direction. The model can be considered to have sufficient span along the first and second directions if the first and second span values both exceed a predetermined threshold value. The span values can be calculated in various ways, such as by using eigenanalysis to decompose the model into a plurality of eigenvectors (corresponding to different directions) and a plurality of eigenvalues (corresponding to the span along the different directions), in accordance with techniques known to those of skill in the art. When calculating the model span, eigenanalysis can provide the directions and/or magnitude of the plan anatomy represented by the model. The eigenanalysis can be performed on a surface model or on a centerline model of the anatomic region. The data from a centerline model may provide a better representation of the directionality and span of the model compared to other types of models. In some embodiments, the eigenanalysis involves calculating a first eigenvalue corresponding to the span along a first direction (e.g., a direction of maximum span such as the superior-inferior direction) and a second eigenvalue corresponding to the span along a second direction (e.g., a direction of minimum span such as the medial-lateral direction). If the first and second eigenvalues both exceed a threshold value, the model is considered to have sufficient span along both the first and second directions. If the first or second eigenvalue is less than the threshold value, the model is considered to have insufficient along the first or second directions, respectively. Alternatively or in combination, other techniques can be used to evaluate model span and/or coverage, such as principal component analysis (PCA), or assessing the area and/or volume contained by a convex hull of the three-dimensional model.

Referring again to FIG. 1, at step 124 the three-dimensional model is analyzed to determine whether it includes key anatomic structures. Specifically, the model should include one or more segmented components corresponding to one or more anatomic structures that are necessary or at least highly beneficial to producing a successful registration. The key anatomic structures for registerability can vary based on the particular anatomy and/or patient, and can be determined based on location, size, shape, distinctiveness, proximity to a target site, and/or other features of the anatomic structures. For example, in embodiments where the anatomic region includes the airways of the lungs, the key anatomic structures can include the trachea, main carina, left main bronchus, right main bronchus, and/or sub-segmental bronchus. A model that lacks segmented components corresponding to some or all of these key anatomic structures may be considered inadequate for registration. In other embodiments, a variety of other anatomic structures may be utilized.

In addition to determining whether certain key anatomic structures are present in the model, the analysis can also include detecting whether the size (e.g., length, diameter, etc.) of these structures as represented in the model is greater than or equal to a predetermined minimum size. For example, in embodiments where the model includes the bronchi of the airways, the analysis can include determining whether the segmented model components corresponding to the bronchi have a length greater than or equal to 0.5 cm, 1 cm, 1.5 cm, 2 cm, 2.5 cm, 3 cm, 3.5 cm, 4 cm, 4.5 cm, or 5 cm. Optionally, the analysis can include assessing other characteristics of the anatomic structures represented in the model. For example, in embodiments where the anatomic structure is a branched structure having a plurality of generations (e.g., a bronchus), the analysis can include detecting whether the model includes a predetermined minimum number of generations (e.g., at least two, three, four, five, six, seven, eight, or more generations).

At step 126, one or more registrations are performed between the three-dimensional model and one or more virtual registration data sets. Each virtual registration data set can be configured to simulate survey data collected by a medical device driven within the anatomic region during an actual registration procedure. For example, the virtual registration data set can simulate sensor data (e.g., positional and/or shape data) generated by one or more sensors in the medical device as the medical device is driven within different passageways in the anatomy. Accordingly, the registration between the virtual registration data set and the model can be used to simulate the results of an actual registration performed between the real patient anatomy and the model.

The simulated registrations can be conducted in variety of different ways, as described in greater detail below with respect to FIGS. 3 and 4. In some embodiments, for example, one or more simulated registrations are performed between the model and a single virtual registration data set, with each registration being performed with a different randomized initial seed. Alternatively or in combination, a plurality of simulated registrations can be performed between the model and a plurality of different virtual registration data sets. To register the model to the virtual registration data set(s), the data points of the virtual registration data set(s) can be rotated, translated, or otherwise manipulated by rigid and/or non-rigid transformations to align them with the data points of the model. The simulated registrations may be performed, for example, using a point-based iterative closest point (ICP) technique, as described in U.S. Provisional Pat. App. Nos. 62/205,440 and No. 62/205,433, which are both incorporated by reference herein in their entireties. In other embodiments, however, the simulated registrations can be performed using other registration techniques.

The registerability of the model can be assessed based on whether the model can be accurately and consistently registered to the virtual registration data set(s). The model may be considered inadequate for registration if the model cannot be accurately registered to the virtual registration data set(s) and/or if the registration results are unstable or inconsistent. As discussed above, the accuracy and stability of the registration can be evaluated across the entire model, or only at selected portions of the model (e.g., model portions representing anatomic locations that contain a target site, or other locations where accurate registration is particularly critical).

At step 130, the evaluation results are output to an operator (e.g., a surgeon or clinician who will be performing the registration procedure). The evaluation results can include the results of each of the analyses of steps 122-126, as well as feedback indicating whether the three-dimensional model is suitable for use in the registration procedure. In some embodiments, the three-dimensional model is considered suitable for registration if steps 122-126 each produce a successful outcome (e.g., the model has sufficient span, includes all key anatomic structures, and can be successfully registered to the virtual registration data set(s)). In other embodiments, however, the model may be considered suitable even if some of steps 122-126 are not successful (e.g., the model does not have sufficient span but includes all key anatomic structures and can be successfully registered to the virtual registration data set(s)). Optionally, the analyses of steps 122-126 can be given different weights in evaluating the overall registerability of the model. In further embodiments, the output can simply include the results of the analyses of steps 122-126 so the operator evaluates the registerability of the model (e.g., based on their own knowledge and experience) without any specific recommendation or guidance from the system.

If the model is considered suitable, the system can provide feedback instructing the operator that the model is ready to be used in the medical procedure. If the model is not considered suitable, the feedback can indicate that corrective action is needed before the procedure is performed, and, optionally, can provide instructions or recommendations on the corrective actions to be taken. For example, the feedback can instruct the operator to collect additional image data of a portion of the anatomic region or of the entire anatomic region. Alternatively or in combination, the feedback can instruct the operator to revise the model, e.g., by segmenting additional anatomic structures from the image data, modifying existing model components, and so on. In some embodiments, the feedback can instruct the operator to expand, refine, or otherwise improve specific portions of the model, for example, if those portions do not include enough data (e.g., the model lacks span along a certain direction and/or is missing certain anatomic structures, etc.) and/or if the simulated registrations are particularly inaccurate or inconsistent at those portions. Subsequently, the analyses of one or more of steps 122-126 can be repeated to evaluate the registerability of the revised model. The evaluation, feedback, and revision processes can be repeated multiple times to iteratively arrive at a suitable model.

Once the three-dimensional model is approved, the method 100 can proceed to step 140 with registering the model to the anatomic region during an actual registration procedure performed in the patient. In some embodiments, the model is saved (e.g., as one or more digital files) as part of a plan for a medical procedure that includes the registration procedure. Optionally, the approved model can be used for other preoperational planning steps for the medical procedure (e.g., determining a survey trajectory for registration, determining a navigation path for a medical device to reach a target site, etc.). In embodiments where the plan is created on a preoperative planning workstation, the plan can be transferred to the medical instrument system used to perform the registration procedure.

During the registration procedure, the three-dimensional model can be displayed to the operator (e.g., via a graphical user interface) for visual guidance as the operator drives the medical device within the anatomic region to obtain survey data. The model can then be registered to the survey data—and thus, the actual patient anatomy—using ICP techniques or any of the other techniques described herein. In some embodiments, the operator can review the registration results, and either accept the registration or take actions to adjust the registration. For example, the operator can obtain additional survey data and re-run the registration algorithm (e.g., using only the new survey data or using survey data combined across multiple survey passes). This process can be repeated multiple times until a satisfactory registration is achieved. Optionally, in embodiments where multiple registrations are performed, a sensitivity analysis can be performed to assess the stability and consistency of the registration results.

Once the registration has been approved, the method 100 can proceed to step 150 with displaying the three-dimensional model during a medical procedure. The model can be used to guide the operator in performing the medical procedure (e.g., navigating a biopsy instrument to a target lesion), as described in greater detail below.

Although the steps of the method 100 are discussed and illustrated in a particular order, a person of ordinary skill in the relevant art will recognize that the method 100 can be altered and still remain within these and other embodiments of the present technology. In other embodiments, for example, the method 100 can be performed in a different order, e.g., any of the steps of the method 100 can be performed before, during, and/or after any of the other steps of the method 100. For example, step 124 can be performed before step 122, step 126 can be performed before step 122 and/or step 124, and so on. Additionally, one or more steps of the method 100 illustrated in FIG. 1 can be omitted. For example, steps 140 and 150 can be omitted, or can be performed by a different system or device than the system or device used to perform steps 110-130. Optionally, one or more steps of the method 100 can be repeated.

Figure 3:
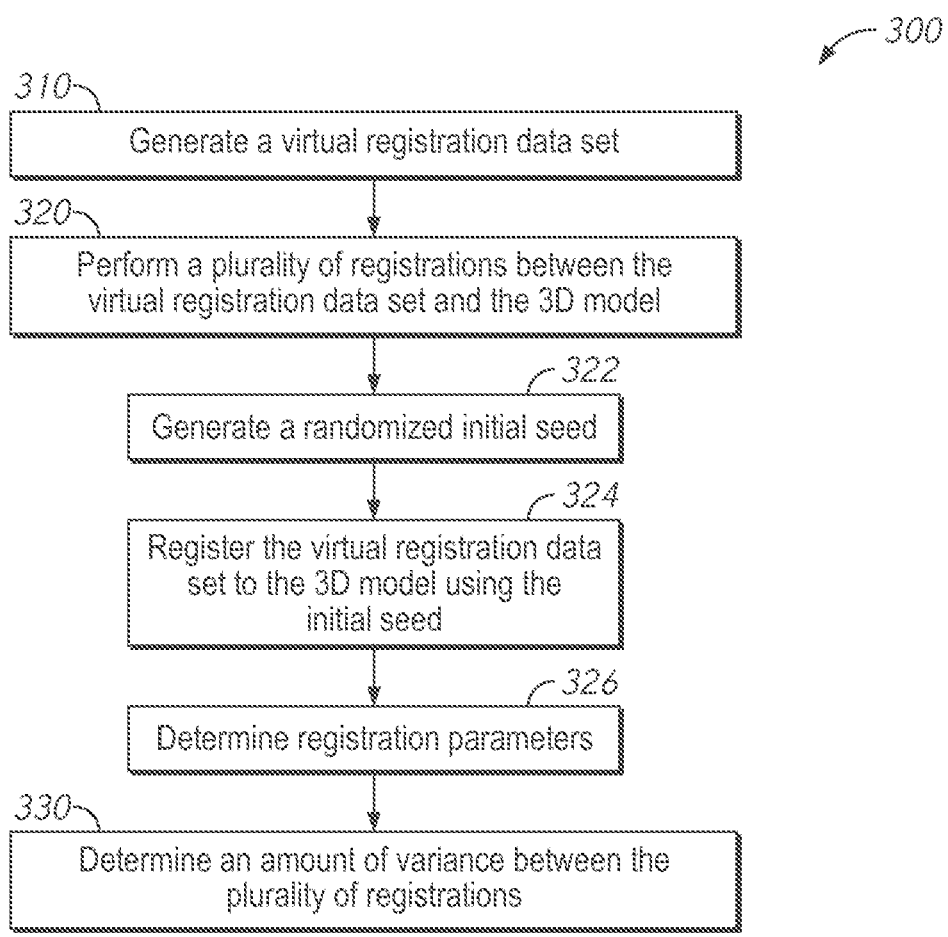
FIG. 3 is a flow diagram illustrating a method for performing registrations between a three-dimensional model and a virtual registration data set in accordance with various embodiments of the present technology.

FIG. 3 is a flow diagram illustrating a method 300 for performing registrations between a three-dimensional model and a virtual registration data set in accordance with various embodiments of the present technology. The method 300 is illustrated as a set of steps or processes 310-330. In some embodiments, some or all of the steps of the method 300 are performed as part of a method for evaluating registerability of the model (e.g., as part of step 126 of the method 100 of FIG. 1). The method 300 can be performed by a suitable computing system or device (e.g., a preoperative planning workstation, a medical instrument system, etc.). The computing system for implementing the method 300 can include one or more processors operably coupled to a memory storing instructions that, when executed, cause the computing system to perform operations in accordance with the steps 310-330.

The method 300 begins at step 310 with generating a virtual registration data set. The virtual registration data set can simulate survey data collected by a medical device during a registration procedure. In some embodiments, the virtual registration data set is generated from the three-dimensional model and includes data points randomized along multiple parameters (e.g., passageways, noise, deformation, depth, etc.). For example, the data points can be generated by selecting a subset of the passageways or structures of the model (e.g., all airways up to the nth generation, airways near a target lesion or other site of interest), creating a skeletonized representation of the centerline of those passageways/structures, and then adding randomized noise to the skeletonized representation to simulate survey data from driving a device within the selected passageways/structures. In other embodiments, the virtual registration data set can be generated by determining a simulated survey trajectory within the three-dimensional model, then selecting randomized data points along or near the survey trajectory to simulate survey data from driving a device along the survey trajectory. Subsequently, the data points can be perturbed (e.g., translated and/or rotated) relative to their original locations so that the virtual registration data set is out of alignment with the model. As another example, the data points can be generated by applying a deformation to the model that represents observed or expected anatomical motion at known locations (e.g., airways). This approach can be used to produce data points that reflect anticipated motion or misalignment that may occur during an actual registration procedure (e.g., due to breathing, physiological factors, patient motion, etc.).

At step 320, a plurality of registrations are performed between the virtual registration data set and the three-dimensional model. The result of each registration can be a set of registration parameters (e.g., translation and/or rotation parameters) that, when applied to the points of the model, align the model to the virtual registration data set. Because the virtual registration data set is generated from the model, the "true" registration parameters for aligning the virtual registration data set and the model are known and can be used to evaluate the accuracy of the simulated registrations. In some embodiments, step 320 involves using Monte Carlo analysis, sensitivity analysis, and/or other suitable techniques to assess whether the model can be consistently and accurately registered to the virtual registration data set.

At step 322, for example, a randomized initial seed is generated. The initial seed can be an initial guess of the registration parameters for aligning the three-dimensional model to the virtual registration data set. For example, in embodiments where the three-dimensional model is a model of the patient's airways, the initial seed can be an estimated transformation for aligning the main carina in the model to the main carina in the virtual registration data set. The randomized initial seed can be generated in various ways, such as by first determining the "true" registration parameters for aligning the model with the registration data set, then adding randomized noise to the parameters. At step 324, the virtual registration data set is registered to the three-dimensional model using the initial seed as a starting point. The registration can be performed using techniques that are identical or similar to techniques for an actual registration procedure (e.g., ICP techniques), as previously described herein. At step 326, the registration parameters for the registration are determined. For example, the output of the registration algorithm can be a transformation matrix describing the translations, rotations, and/or other transformation or manipulations to map the model onto the virtual registration data set. In some embodiments, to create a sufficient set of results for Monte Carlo analysis or other statistical analysis, steps 322-326 are repeated multiple times (e.g., at least 5, 10, 20, or 50 times) with a different randomized initial seed for each simulated registration.

At step 330, the method 300 determines an amount of variance between the plurality of registrations. The variance can be determined, for example, by performing statistical analysis on the registration parameters from each simulated registration to assess the spread between the parameters. Alternatively or in combination, statistical analysis can be used to assess the spread between the accuracy of each registration. The amount of variance can correlate to the overall registration stability of the model. For example, if the variance between registrations is relatively low (e.g., less than or equal to a threshold value), the model may be more likely to produce a stable and successful registration during the actual registration procedure. Conversely, if the variance between registration is relatively large (e.g., greater than a threshold value), the model may be less likely to produce a stable and successful registration. These results can be used to evaluate the overall registerability of the model, as previously described with respect to step 120 of the method 100 of FIG. 1. The results can also be output to the operator as feedback for revising the model. Statistical measures of variance may be computed as a whole to determine registrability of the entire model, or can be computed for a specific location within the model (e.g., a location corresponding to a lesion or other site of interest in the anatomic region).

Although the steps of the method 300 are discussed and illustrated in a particular order, a person of ordinary skill in the relevant art will recognize that the method 300 can be altered and still remain within these and other embodiments of the present technology. In other embodiments, for example, the method 300 can be performed in a different order, e.g., any of the steps of the method 300 can be performed before, during, and/or after any of the other steps of the method 300. Additionally, one or more steps of the method 300 illustrated in FIG. 3 can be omitted or repeated.

Figure 4:
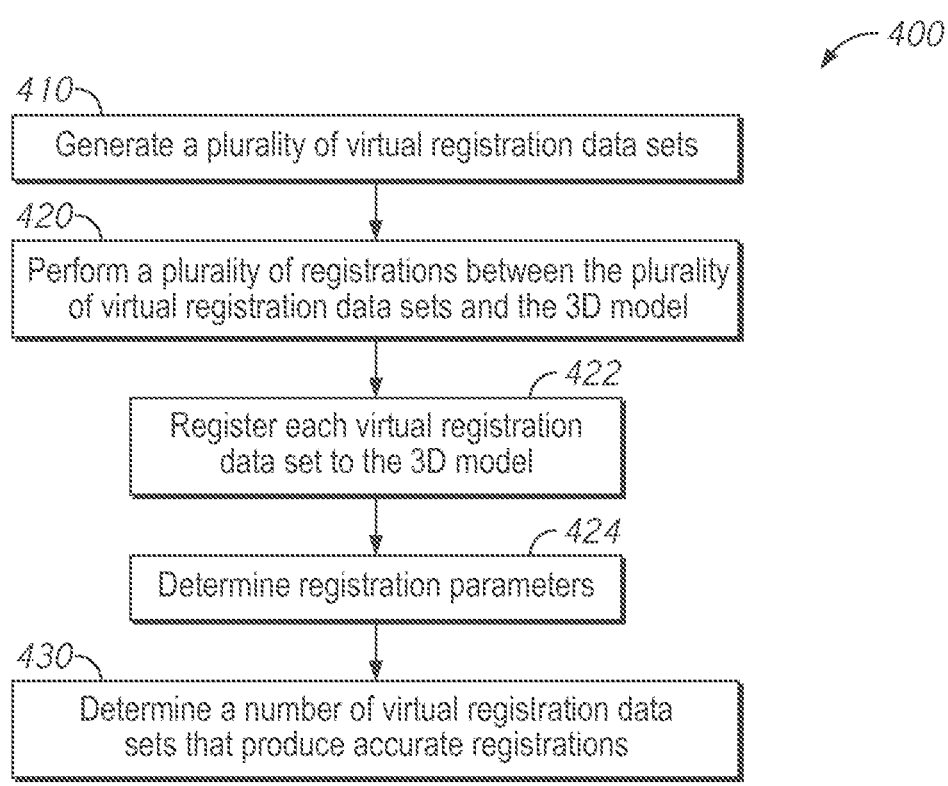
FIG. 4 is a flow diagram illustrating a method for performing registrations between a three-dimensional model and a plurality of virtual registration data sets in accordance with various embodiments of the present technology.

FIG. 4 is a flow diagram illustrating a method 400 for performing registrations between a three-dimensional model and a plurality of virtual registration data sets in accordance with various embodiments of the present technology. The method 400 is illustrated as a set of steps or processes 410-430. In some embodiments, some or all of the steps of the method 400 are performed as part of a method for evaluating registerability of the model (e.g., as part of step 126 of the method 100 of FIG. 1). For example, the method 400 can be performed in combination with or as an alternative to the method 300 of FIG. 3. The method 400 can differ from the method 300 in that the method 300 involves repeatedly registering the model to a single virtual registration data set with different initial seeds for each registration run, while the method 400 involves registering the model to multiple different virtual registration data sets. The method 400 can be performed by a suitable computing system or device (e.g., a preoperative planning workstation, a medical instrument system, etc.). The computing system for implementing the method 400 can include one or more processors operably coupled to a memory storing instructions that, when executed, cause the computing system to perform operations in accordance with the steps 410-430.

The method 400 begins at step 410 with generating a plurality of virtual registration data sets. Each virtual registration data set can simulate survey data collected by a medical device during a registration procedure. In some embodiments, each virtual registration data set is different from the other data sets. For example, step 410 involves generating at least 5, 10, 20, 50, or more different virtual registration data sets. The different virtual registration data sets can be generated from the model using techniques similar or identical to the processes described with respect to step 310 of the method 300 of FIG. 3. In some embodiments, for example, each virtual registration data set is generated from a different portion of the model (e.g., different airways). Alternatively, some or all of the virtual registration data sets can be generated from the same portion of the model, but with randomized noise added so that each set includes at least some unique data points. Optionally, some or all of the virtual registration data sets can be generated based on different simulated survey trajectories, as previously described with respect to step 310 of FIG. 3.

At step 420, a plurality of registrations is performed between the virtual registration data sets and the three-dimensional model. In some embodiments, each registration is performed between the model and a different virtual registration data set. The result of each registration can be a set of registration parameters that align the model to the respective virtual registration data set. For example, at step 422, a virtual registration data set is registered to the three-dimensional model. The registration can be performed using techniques that are identical or similar to techniques for an actual registration procedure (e.g., ICP techniques), as previously described herein. At step 424, the registration parameters for the registration are determined, as previously described. Steps 422 and 424 can be repeated multiple times until all of the virtual registration data sets have been registered with the model.

At step 430, the method 400 determines a number of virtual registration data sets that produced accurate registrations with the model. As previously described, because each virtual registration data set is generated from the model, the "true" registration parameters for each virtual registration data are already known. Accordingly, the registration parameters for each virtual registration data set can be compared to the "true" parameters to determine the accuracy of the registration. In some embodiments, the accuracy can be expressed as a score or other quantitative measurement. The method 400 can then determine the number and/or proportion of simulated registrations that produced a sufficiently accurate result (e.g., the accuracy score for the registration is greater than or equal to a threshold value). The number and/or proportion of accurate registrations can correlate to the overall likelihood that the model will be successfully registered to the anatomy during the actual registration procedure. For example, the model can be considered suitable for registration if there was at least one virtual registration data set that produced an accurate registration, or if at least 50%, 75%, 80%, 90%, 95%, or 99% of the simulated registration results were sufficiently accurate. Conversely, the model can be considered inadequate for registration if there were no virtual registration data sets that produced an accurate registration, or if the number and/or proportion of accurate registrations is too small (e.g., less than 50%, 25%, 10%, or 5% accurate registrations). As discussed above, the accuracy of the simulated registrations can be evaluated across the entire model, or can be evaluated only for selected portions of the model (e.g., portions corresponding to a target anatomical site of interest). These results can be used to evaluate the overall registerability of the model, as previously described with respect to step 120 of the method 100 of FIG. 1. The results can also be output to the operator as feedback for revising the model.

Optionally, the method 400 can include other techniques for assessing the overall stability and accuracy of the simulated registrations. In some embodiments, for example, the method 400 includes performing statistical analysis on the registration results to determine the variance or spread in accuracy across all registrations. The method 400 can also include identifying common characteristics in virtual registration data sets that produced successful or unsuccessful registrations (e.g., if virtual registration data sets generated from certain portions of the model tended to produce more accurate or inaccurate registrations). This information can be provided to the operator as additional feedback for adjusting the model.

Although the steps of the method 400 are discussed and illustrated in a particular order, a person of ordinary skill in the relevant art will recognize that the method 400 can be altered and still remain within these and other embodiments of the present technology. In other embodiments, for example, the method 400 can be performed in a different order, e.g., any of the steps of the method 400 can be performed before, during, and/or after any of the other steps of the method 400. Additionally, one or more steps of the method 400 illustrated in FIG. 4 can be omitted or repeated.

In some embodiments, the three-dimensional anatomic models described herein are used to plan a registration procedure. As previously described, the registration procedure can involve driving a medical device within passageways of an anatomic region to collect survey data, then registering the model to the anatomic region using the survey data. However, the operator may not know the optimal trajectory or route for driving the medical device to obtain survey data. Even if the system instructs the operator to drive the device within certain areas of the anatomy, it may be difficult to determine the specific passageways that the device should be driven into, particularly when the passageways are extremely dense or tortuous (e.g., as in the airways of the lungs). Additionally, the operator may not know whether they have collected enough survey data to produce an accurate and consistent registration with the model. In some instances, even if the model itself is suitable for registration, the registration may nevertheless fail if not enough survey data is obtained and/or if the locations covered by the survey data are not ideal. Accordingly, in some embodiments, the systems described herein are configured to plan survey trajectories that are likely to produce a successful registration to the model. The survey trajectories can be displayed to guide the operator in collecting survey data during the registration procedure.

Figure 5:
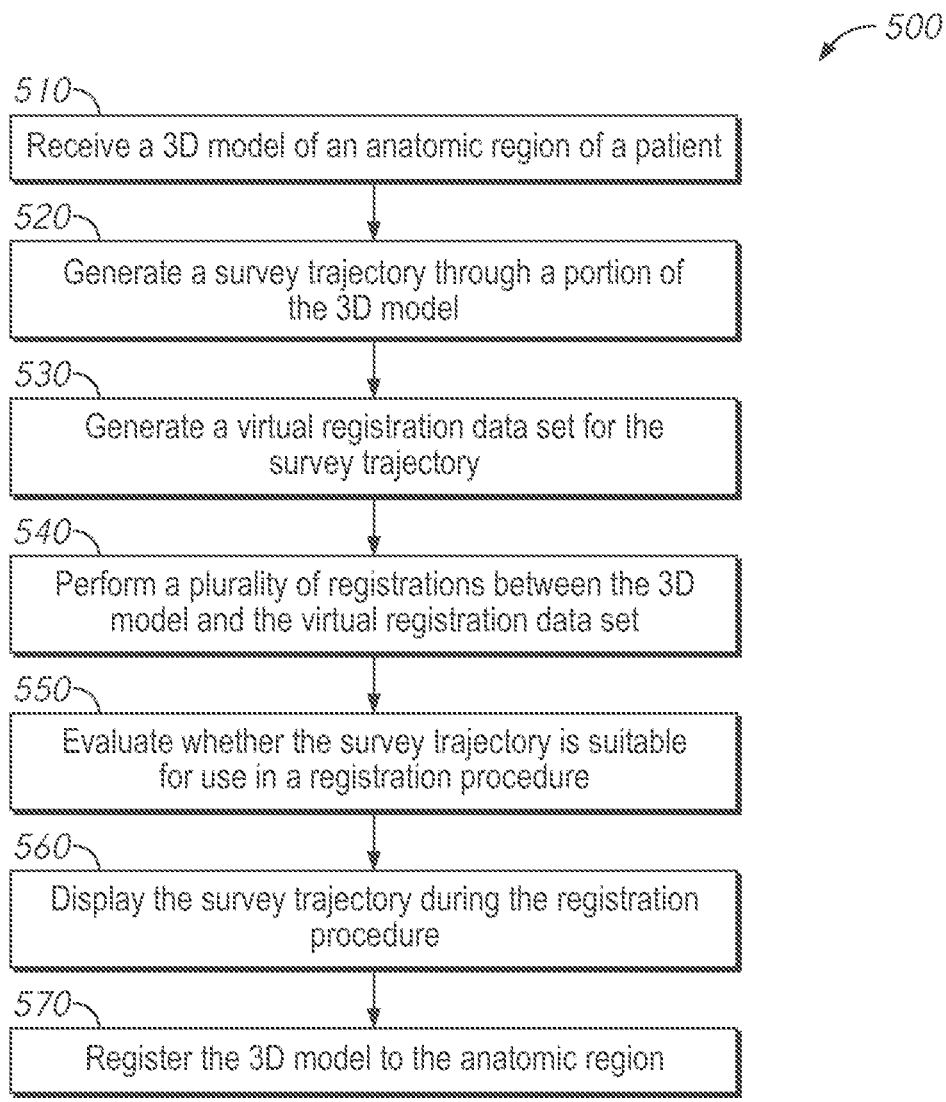
FIG. 5 is a flow diagram illustrating a method for planning a registration procedure in accordance with various embodiments of the present technology.

FIG. 5 is a flow diagram illustrating a method 500 for planning a registration procedure in accordance with various embodiments of the present technology. The method 500 is illustrated as a set of steps or processes 510-570. The method 500 can be performed by a suitable computing system or device (e.g., a preoperative planning workstation, a medical instrument system, etc.). The computing system for implementing the method 500 can include one or more processors operably coupled to a memory storing instructions that, when executed, cause the computing system to perform operations in accordance with the steps 510-570.

The method 500 begins at step 510 with receiving a three-dimensional model of an anatomic region of a patient. The model can be a segmented model generated from preoperative imaging data, as previously described with respect to step 110 of the method 100 of FIG. 1. In some embodiments, the model has already been determined to be suitable for registration, as previously described with respect to the methods 100, 300, and/or 400 of FIGS. 1, 3, and 4, respectively. In other embodiments, the registerability of the model has not yet been evaluated, such that some or all of the subsequent steps of the method 500 (e.g., steps 520-550) can be performed before or concurrently with some or all of the steps of the methods 100, 300, and/or 400.

At step 520, a survey trajectory through a portion of the three-dimensional model is generated. The survey trajectory can be a proposed route for driving a medical device within the anatomic region to collect survey data during a registration procedure. The survey trajectory can be generated automatically, semi-automatically, or manually using the model. For example, an operator can manually create some or all of the survey trajectory by selecting passageways (e.g., airways) within the model via a suitable graphical user interface. Alternatively or in combination, some or all of the survey trajectory can be generated automatically by the system. In some embodiments, the system can automatically generate a trajectory, and the operator can either approve the trajectory or manually revise the trajectory (e.g., by adding, deleting, or otherwise modifying portions of the trajectory). Conversely, the operator can manually create a trajectory, and the system can automatically revise the trajectory or propose revisions for approval by the operator.

In some embodiments, the system automatically identifies passageways in the model that, when surveyed with the medical device, are likely to produce an accurate registration, and generates a survey trajectory that traverses some or all of these passageways. For example, the system can select passageways based on accessibility to the medical device (e.g., sufficiently large diameter, not too tortuous), depth within the anatomic region (e.g., at least x generations deep), and/or distinctiveness (e.g., having a shape and/or location that can be readily distinguished from other passageways). Optionally, the survey trajectory can be generated based at least in part on patient-specific factors, such as a location of a target site for the medical procedure (e.g., a target lesion or biopsy site). For instance, the survey trajectory can be configured to traverse passageways that are located relatively close to the target site to increase the likelihood that the registration will be accurate at or near the target site. Optionally, if the target site is at a particular depth within the anatomic region (e.g., at or near an nth generation passageway), the survey trajectory can be configured to be at least deep as the as the target site to increase the likelihood that the registration will be accurate at the target depth.

At step 530, a virtual registration data set is generated for the survey trajectory. The virtual registration data set can simulate survey data produced by a medical device driven along the survey trajectory, and can include a plurality of data points along or near the survey trajectory. The virtual registration data set can be generated using techniques identical or similar to the techniques previously described with respect to steps 310 and/or 410 of FIGS. 3 and 4, respectively. In some embodiments, for example, the system creates a skeletonized representation of the centerlines of the passageways traversed by the survey trajectory, then adds randomized noise to the representation to generate the data points for the virtual registration data set. In other embodiments, a deformation can be applied to the model that simulates or is representative of anticipated anatomical motion at certain locations (e.g., airways) to generate data points that reflect anticipated motion or misalignment (e.g., due to breathing, physiological factors, or patient motion).

At step 540, a plurality of registrations is performed between the three-dimensional model and the virtual registration data set (e.g., at least 5, 10, 20, 50, or more registrations). Similar to the method 300 of FIG. 3, this step can use Monte Carlo analysis, sensitivity analysis, and/or other statistical techniques to assess whether the virtual registration data set generated from the survey trajectory consistently produces an accurate registration to the model. In some embodiments, the registration algorithm includes some or all of processes described with respect to steps 322-326 of the method 300 of FIG. 3. For example, each registration can be performed using the same virtual registration data set and a different (e.g., randomized) initial seed. Each registration can produce a set of registration parameters representing the estimated transformation for mapping the three-dimensional model onto the virtual registration data set.

At step 550, the system evaluates whether the survey trajectory is suitable for use in a registration procedure, based on the registration results from step 540. The evaluation can include determining an amount of variance between the registrations, similar to the process described above with respect to step 330 of the method 300 of FIG. 3. If the amount of variance is relatively low (e.g., less than or equal to a threshold value), the survey trajectory may be more likely to produce an accurate registration to the model. On the other hand, if the amount of variance is relatively high (e.g., greater than a threshold value), the survey trajectory may be less likely to produce an accurate registration.

If the survey trajectory is determined to be inadequate for registration, the system can output feedback to the operator indicating that corrective actions are needed, and, optionally, can include instructions or recommendations on the specific corrective actions to be taken. For example, the feedback can instruct the operator to manually add, delete, or otherwise revise portions of the survey trajectory. In some embodiments, if the registration accuracy at certain locations in the model is particularly poor, the system can instruct the operator to extend the survey trajectory into those locations. Subsequently, the analyses of steps 530-550 can be repeated to evaluate whether the revised survey trajectory produces satisfactory registration results. The evaluation, feedback, and revision processes can be repeated multiple times to iteratively arrive at a suitable survey trajectory.

Once the survey trajectory is determined to be suitable, the method 500 can proceed to step 560 with displaying the survey trajectory during a registration procedure. In some embodiments, the survey trajectory is saved (e.g., as one or more digital files) as part of a preoperative plan for a medical procedure that includes the registration procedure. The plan can also include the three-dimensional model used to generate survey trajectory. The plan can be transferred to a medical instrument system that is to be used to perform the medical procedure. Examples of medical instrument systems suitable for use with the embodiments herein are described in greater detail below.

During the registration procedure, the survey trajectory can be displayed to the operator (e.g., via a graphical user interface) to provide visual guidance for driving a medical device within the patient anatomy to collect survey data. For example, the system can output a graphical representation of the survey trajectory, e.g., as a path overlaid onto the model and/or images of the actual patient anatomy. Alternatively or in combination, the system can output textual, audio, or other instructions that direct the operator to navigate the device along the survey trajectory (e.g., in a particular direction and/or for a particular distance, with respect to particular anatomic landmarks, etc.). Optionally, the system can display the survey trajectory along with positional data of the medical device collected by the medical device so that operator can track the location of the device relative to the trajectory. In some embodiments, the system also displays the survey data collected by the medical device along with the survey trajectory so the operator can assess whether sufficient data has been obtained, whether there are any gaps or areas of incomplete sampling, etc.

At step 570, the three-dimensional model is registered to the anatomic region using the survey data collected during the registration procedure (e.g., as previously described with respect to step 140 of the method 100 of FIG. 1). In some embodiments, the survey trajectory is also used in computing the registration. For example, when calculating the registration parameters, the registration algorithm can assume that the survey data is located along or near the survey trajectory. Optionally, the algorithm can disregard survey data points that are located away from the survey trajectory when computing the registration, e.g., if such data points are deemed unnecessary for an accurate registration and/or likely to introduce errors. In some embodiments, the operator reviews the registration results, and, if desired, collects additional survey data to revise the registration, as discussed above with respect to step 140 of FIG. 1. Once the model has been successfully registered to the patient anatomy, the model can be used to guide the operator in performing a medical procedure (e.g., navigating a biopsy instrument to a target lesion), as described in greater detail below.

Although the steps of the method 500 are discussed and illustrated in a particular order, a person of ordinary skill in the relevant art will recognize that the method 500 can be altered and still remain within these and other embodiments of the present technology. In other embodiments, for example, the method 500 can be performed in a different order, e.g., any of the steps of the method 500 can be performed before, during, and/or after any of the other steps of the method 100. Additionally, one or more steps of the method 500 illustrated in FIG. 1 can be omitted. For example, steps 560 and 570 can be omitted, or can be performed by a different system or device than the system or device used to perform steps 510-550.

Optionally, one or more steps of the method 500 can be repeated. For example, steps 520-550 can be repeated multiple times to generate and evaluate a plurality of different survey trajectories (e.g., two, three, four, five, or more different survey trajectories). The different survey trajectories can differ from each other with respect to location within the anatomic region, proximity to a target site in the anatomic region, length, depth, shape, distinctiveness, and/or any other suitable characteristic. For example, the systems described herein can evaluate multiple survey trajectories and suggest different trajectories, depending on the location of a target lesion for a subsequent biopsy procedure. A virtual registration data set can be generated for each survey trajectory and used in a simulated registration to evaluate the suitability of the survey trajectory, as described above. In such embodiments, the method 500 can further include selecting a subset of the survey trajectories for use in the registration procedure, e.g., based on whether the survey trajectories are likely to produce an accurate and stable registration. The selected trajectories can be sequentially or simultaneously displayed to the operator at step 560 so the operator can choose between different options for the actual registration procedure.

Moreover, in other embodiments, rather than generating a single virtual registration data set for each survey trajectory, steps 530 and 540 can be repeated multiple times for a single survey trajectory to generate a plurality of different virtual registration data sets for that trajectory (e.g., at least 5, 10, 20, 50, or more data sets). The different virtual registration data sets can be created using the techniques previously described with respect to step 410 of the method 400 of FIG. 4. The suitability of the survey trajectory for registration can then be determined by assessing the number and/or proportion of the virtual registration data sets that can be successfully registered to the model, similar to the techniques previously described with respect to steps 420-430 of the method 400 of FIG. 4. This approach may provide additional information regarding the quality and stability of the registrations produced via the survey trajectory.

In some embodiments, the techniques for determining a survey trajectory for a registration procedure can be combined with the techniques for evaluating registerability of a three-dimensional anatomic model. For example, some or all of the steps of the method 500 of FIG. 5 can be combined or performed concurrently with some or all of the steps of the method 100 of FIG. 1 (e.g., step 110 of method 100 can be combined with step 510 of method 500, step 126 of method 100 can be combined with steps 520-540 of method 500, step 140 of method 100 can be combined with step 560 and 570 of method 500, and so on). In such embodiments, the method 500 can be performed partly or entirely by the same system or device used to perform the method 100, or vice-versa. In other embodiments, however, the method 500 and method 100 can be distinct processes that are performed at different times and/or by different systems or devices.

In some embodiments, the techniques described herein with respect to FIGS. 1-5 are performed as part of preoperative planning for a medical procedure to biopsy one or more target sites (e.g., lesions or other tissues of interest). As such, the techniques described herein can be used to (i) evaluate the registerability of the anatomic model to the anatomy at or near the target site(s) and (ii) determine one or more survey trajectories that are likely to produce accurate and consistent registrations to the anatomy at or near the target site(s). In embodiments where the medical procedure involves biopsying multiple target sites, the systems described herein can assess the registerability of the model with respect to each target site (e.g., by analyzing model span, key anatomic structures, and/or simulated registration outcomes at or near each site), and/or can propose survey trajectories customized to each site (e.g., by evaluating different survey trajectories through portions of the anatomy at or near each site).

B. EMBODIMENTS OF ROBOTIC OR TELEOPERATED MEDICAL SYSTEMS AND ASSOCIATED DEVICES, SYSTEMS, AND METHODS

Figure 6:
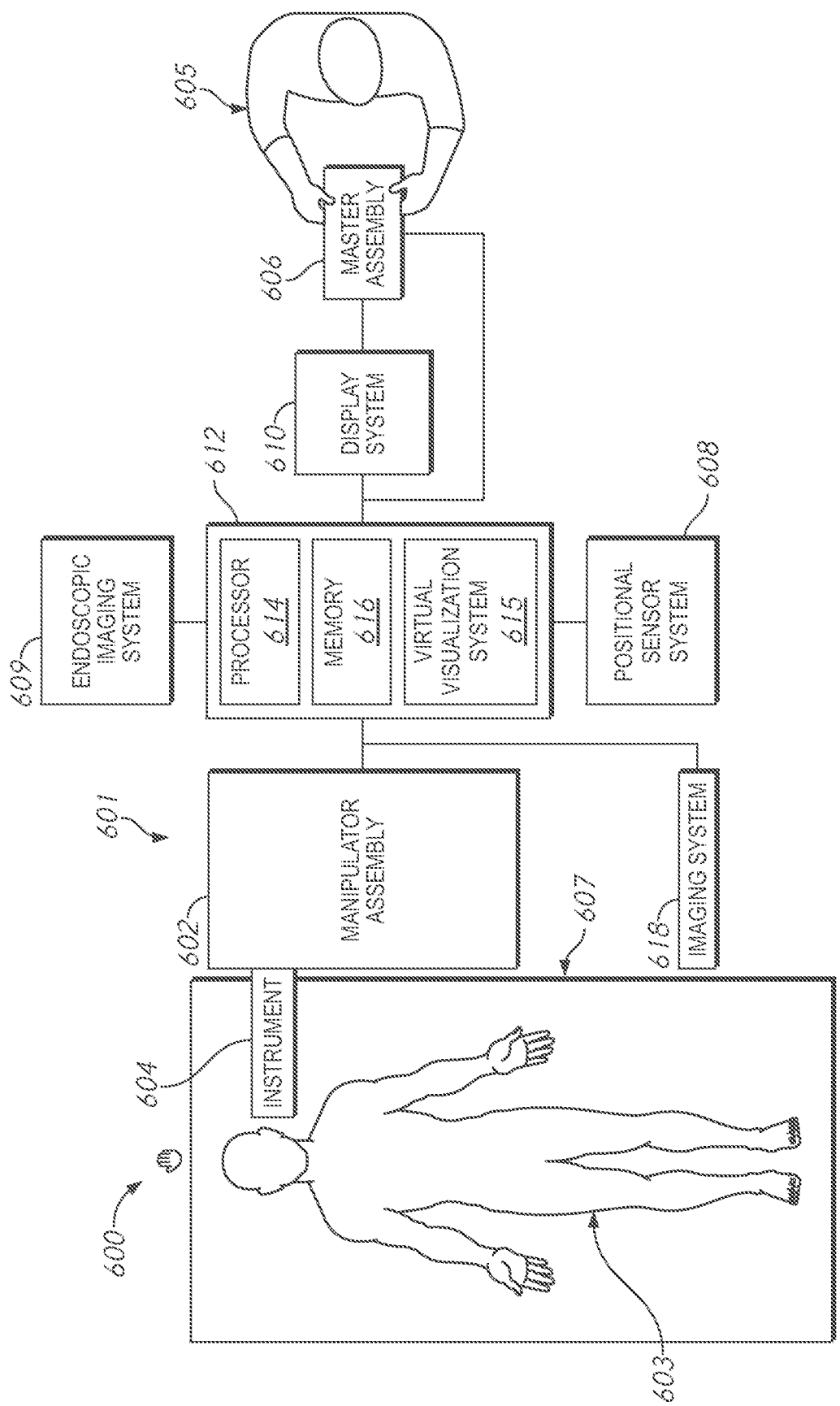
FIG. 6 is a schematic representation of a robotic or teleoperated medical system configured in accordance with various embodiments of the present technology.

FIG. 6 is a schematic representation of a robotic or teleoperated medical system 600 ("medical system 600") configured in accordance with various embodiments of the present technology. The medical system 600 can be used with any of the procedures or methods described above with respect to FIGS. 1-5. As shown, the medical system 600 includes a manipulator assembly 602, a medical instrument system 604, a master assembly 606, and a control system 612. The manipulator assembly 602 supports the medical instrument system 604 and drives the medical instrument system 604 at the direction of the master assembly 606 and/or the control system 612 to perform various medical procedures on a patient 603 positioned on a table 607 in a surgical environment 601. In this regard, the master assembly 606 generally includes one or more control devices that can be operated by an operator 605 (e.g., a physician) to control the manipulator assembly 602. Additionally, or alternatively, the control system 612 includes a computer processor 614 and at least one memory 616 for effecting control between the medical instrument system 604, the master assembly 606, and/or other components of the medical system 600. The control system 612 can also include programmed instructions (e.g., a non-transitory computer-readable medium storing the instructions) to implement any one or more of the methods described herein, including instructions for providing information to a display system 610 and/or processing data for registration of the medical instrument system 604 with an anatomical model of the patient 603 (as described in greater detail below). The manipulator assembly 602 can be a teleoperated, a non-teleoperated, or a hybrid teleoperated and non-teleoperated assembly. Thus, all or a portion of the master assembly 606 and/or all or a portion of the control system 612 can be positioned inside or outside of the surgical environment 601.

To aid the operator 605 in controlling the manipulator assembly 602 and/or the medical instrument system 604 during an image-guided medical procedure, the medical system 600 may further include a positional sensor system 608, an endoscopic imaging system 609, an imaging system 618, and/or a virtual visualization system 615. In some embodiments, the positional sensor system 608 includes a location sensor system (e.g., an electromagnetic (EM) sensor system) and/or a shape sensor system for capturing positional sensor data (e.g., position, orientation, speed, velocity, pose, shape, etc.) of the medical instrument system 604. In these and other embodiments, the endoscopic imaging system 609 includes one or more image capture devices (not shown) that record endoscopic image data that includes concurrent or real-time images (e.g., video, still images, etc.) of patient anatomy. Images captured by the endoscopic imaging system 609 may be, for example, two or three-dimensional images of patient anatomy captured by an image capture device positioned within the patient 603, and are referred to hereinafter as "real navigational images."

In some embodiments, the medical instrument system 604 may include components of the positional sensor system 608 and/or components of the endoscopic imaging system 609. For example, components of the positional sensor system 608 and/or components of the endoscopic imaging system 609 can be integrally or removably coupled to the medical instrument system 604. Additionally, or alternatively, the endoscopic imaging system 609 can include a separate endoscope (not shown) attached to a separate manipulator assembly (not shown) that can be used in conjunction with the medical instrument system 604 to image patient anatomy. The positional sensor system 608 and/or the endoscopic imaging system 609 may be implemented as hardware, firmware, software, or a combination thereof that interact with or are otherwise executed by one or more computer processors, such as the computer processor(s) 614 of the control system 612.

The imaging system 618 of the medical system 600 may be arranged in the surgical environment 601 near the patient 603 to obtain real-time and/or near real-time images of the patient 603 before, during, and/or after a medical procedure. In some embodiments, the imaging system 618 includes a mobile C-arm cone-beam CT imaging system for generating three-dimensional images. For example, the imaging system 618 can include a DynaCT imaging system from Siemens Corporation, or another suitable imaging system. In these and other embodiments, the imaging system 618 can include other imaging technologies, including MRI, fluoroscopy, thermography, ultrasound, OCT, thermal imaging, impedance imaging, laser imaging, nanotube X-ray imaging, and/or the like.

The virtual visualization system 615 of the control system 612 provides navigation and/or anatomy-interaction assistance to the operator 605 when controlling the medical instrument system 604 during an image-guided medical procedure. As described in greater detail below, virtual navigation using the virtual visualization system 615 can be based, at least in part, upon reference to an acquired pre-operative or intra-operative dataset (e.g., based, at least in part, upon reference to data generated by the positional sensor system 608, the endoscopic imaging system 609, and/or the imaging system 618) of anatomic passageways of the patient 603. In some implementations, for example, the virtual visualization system 615 processes preoperative and/or intraoperative image data of an anatomic region of the patient 603 captured by the imaging system 618 to generate an anatomic model (not shown) of the anatomic region. The virtual visualization system 615 then registers the anatomic model to positional sensor data generated by the positional sensor system 608 and/or to endoscopic image data generated by the endoscopic imaging system 609 to (i) map the tracked position, orientation, pose, shape, and/or movement of the medical instrument system 604 within the anatomic region to a correct position within the anatomic model, and/or (ii) determine a virtual navigational image of virtual patient anatomy of the anatomic region from a viewpoint of the medical instrument system 604 at a location within the anatomic model corresponding to a location of the medical instrument system 604 within the patient 603.

The display system 610 can display various images or representations of patient anatomy and/or of the medical instrument system 604 that are generated by the positional sensor system 608, by the endoscopic imaging system 609, by the imaging system 618, and/or by the virtual visualization system 615. In some embodiments, the display system 610 and/or the master assembly 606 may be oriented so the operator 605 can control the manipulator assembly 602, the medical instrument system 604, the master assembly 606, and/or the control system 612 with the perception of telepresence.

As discussed above, the manipulator assembly 602 drives the medical instrument system 604 at the direction of the master assembly 606 and/or the control system 612. In this regard, the manipulator assembly 602 can include select degrees of freedom of motion that may be motorized and/or teleoperated and select degrees of freedom of motion that may be non-motorized and/or non-teleoperated. For example, the manipulator assembly 602 can include a plurality of actuators or motors (not shown) that drive inputs on the medical instrument system 604 in response to commands received from the control system 612. The actuators can include drive systems (not shown) that, when coupled to the medical instrument system 604, can advance the medical instrument system 604 into a naturally or surgically created anatomic orifice. Other drive systems may move a distal portion (not shown) of the medical instrument system 604 in multiple degrees of freedom, which may include three degrees of linear motion (e.g., linear motion along the X, Y, Z Cartesian axes) and three degrees of rotational motion (e.g., rotation about the X, Y, Z Cartesian axes). Additionally, or alternatively, the actuators can be used to actuate an articulable end effector of the medical instrument system 604 (e.g., for grasping tissue in the jaws of a biopsy device and/or the like).

Figure 7:
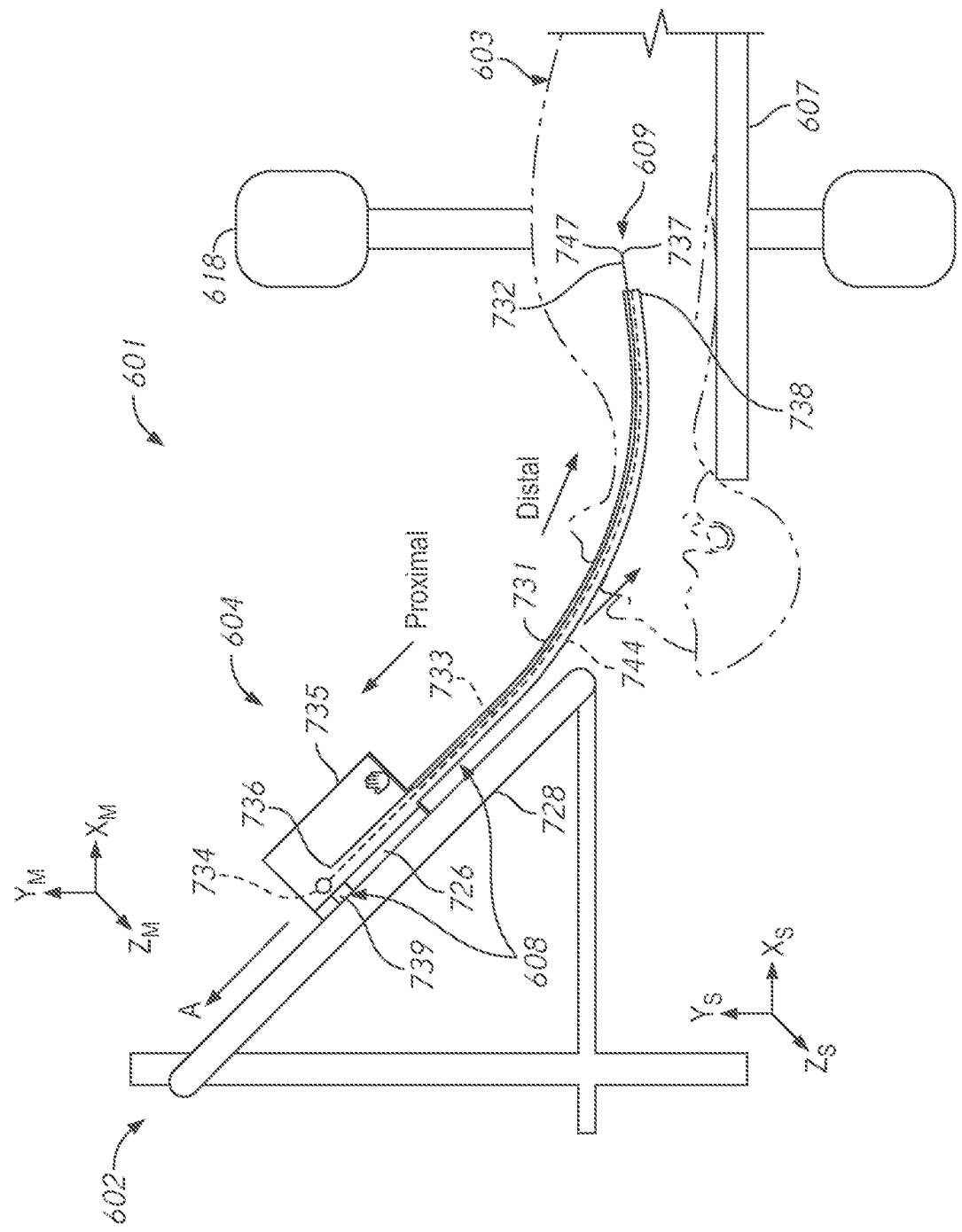
FIG. 7 is a schematic representation of a manipulator assembly, a medical instrument system, and an imaging system configured in accordance with various embodiments of the present technology.

FIG. 7 is a schematic representation of the manipulator assembly 602, the medical instrument system 604, and the imaging system 618 of FIG. 6 within the surgical environment 601 and configured in accordance with various embodiments of the present technology. As shown in FIG. 7, the surgical environment 601 has a surgical frame of reference ($X_S$, $Y_S$, $Z_S$) in which the patient 603 is positioned on the table 607, and the medical instrument system 604 has a medical instrument frame of reference ($X_M$, $Y_M$, $Z_M$) within the surgical environment 601. During the medical procedure, the patient 603 may be stationary within the surgical environment 601 in the sense that gross patient movement can be limited by sedation, restraint, and/or other means. In these and other embodiments, cyclic anatomic motion of the patient 603, including respiration and cardiac motion, may continue unless the patient 603 is asked to hold his or her breath to temporarily suspend respiratory motion.

The manipulator assembly 602 includes an instrument carriage 726 mounted to an insertion stage 728. In the illustrated embodiment, the insertion stage 728 is linear, while in other embodiments, the insertion stage 728 is curved or has a combination of curved and linear sections. In some embodiments, the insertion stage 728 is fixed within the surgical environment 601. Alternatively, the insertion stage 728 can be movable within the surgical environment 601 but have a known location (e.g., via a tracking sensor (not shown) or other tracking device) within the surgical environment 601. In these alternatives, the medical instrument frame of reference ($X_M$, $Y_M$, $Z_M$) is fixed or otherwise known relative to the surgical frame of reference ($X_S$, $Y_S$, $Z_S$).

The medical instrument system 604 of FIG. 7 includes an elongate device 731, a medical instrument 732, an instrument body 735, at least a portion of the positional sensor system 608, and at least a portion of the endoscopic imaging system 609. In some embodiments, the elongate device 731 is a flexible catheter or other biomedical device that defines a channel or lumen 744. The channel 744 can be sized and shaped to receive the medical instrument 732 (e.g., via a proximal end 736 of the elongate device 731 and/or an instrument port (not shown)) and facilitate delivery of the medical instrument 732 to a distal portion 738 of the elongate device 731. The elongate device 731 is coupled to the instrument body 735, which in turn is coupled and fixed relative to the instrument carriage 726 of the manipulator assembly 602.

In operation, the manipulator assembly 602 can control insertion motion (e.g., proximal and/or distal motion along an axis A) of the elongate device 731 into the patient 603 via a natural or surgically created anatomic orifice of the patient 603 to facilitate navigation of the elongate device 731 through anatomic passageways of an anatomic region of the patient 603 and/or to facilitate delivery of a distal portion 738 of the elongate device 731 to or near a target location within the patient 603. For example, the instrument carriage 726 and/or the insertion stage 728 may include actuators (not shown), such as servomotors, that facilitate control over motion of the instrument carriage 726 along the insertion stage 728. Additionally, or alternatively, the manipulator assembly 602 in some embodiments can control motion of the distal portion 738 of the elongate device 731 in multiple directions, including yaw, pitch, and roll rotational directions (e.g., to navigate patient anatomy). To this end, the elongate device 731 may house or include cables, linkages, and/or other steering controls (not shown) that the manipulator assembly 602 can use to controllably bend the distal portion 738 of the elongate device 731. For example, the elongate device 731 can house at least four cables that can be used by the manipulator assembly 602 to provide (i) independent "up-down" steering to control a pitch of the distal portion 738 of the elongate device 731 and (ii) independent "left-right" steering of the elongate device 731 to control a yaw of the distal portion 738 of the elongate device 731.

The medical instrument 732 of the medical instrument system 604 can be used for medical procedures, such as for survey of anatomic passageways, surgery, biopsy, ablation, illumination, irrigation, and/or suction. Thus, the medical instrument 732 can include image capture probes, biopsy instruments, laser ablation fibers, and/or other surgical, diagnostic, and/or therapeutic tools. For example, the medical instrument 732 can include an endoscope or other biomedical device having one or more image capture devices 747 positioned at a distal portion 737 of and/or at other locations along the medical instrument 732. In these embodiments, an image capture device 747 can capture one or more real navigational images or video (e.g., a sequence of one or more real navigational image frames) of anatomic passageways and/or other real patient anatomy while the medical instrument 732 is within an anatomic region of the patient 603.

As discussed above, the medical instrument 732 can be deployed into and/or be delivered to a target location within the patient 603 via the channel 744 defined by the elongate device 731. In embodiments in which the medical instrument 732 includes an endoscope or other biomedical device having an image capture device 747 at its distal portion 737, the image capture device 747 can be advanced to the distal portion 738 of the elongate device 731 before, during, and/or after the manipulator assembly 602 navigates the distal portion 738 of the elongate device 731 to a target location within the patient 603. In these embodiments, the medical instrument 732 can be used as a survey instrument to capture real navigational images of anatomic passageways and/or other real patient anatomy, and/or to aid an operator (not shown) to navigate the distal portion 738 of the elongate device 731 through anatomic passageways to the target location.

As another example, after the manipulator assembly 602 positions the distal portion 738 of the elongate device 731 proximate a target location within the patient 603, the medical instrument 732 can be advanced beyond the distal portion 738 of the elongate device 731 to perform a medical procedure at the target location. Continuing with this example, after all or a portion of the medical procedure at the target location is complete, the medical instrument 732 can be retracted back into the elongate device 731 and, additionally or alternatively, be removed from the proximal end 736 of the elongate device 731 or from another instrument port (not shown) along the elongate device 731.

As shown in FIG. 7, the positional sensor system 608 of the medical instrument system 604 includes a shape sensor 733 and a position measuring device 739. In these and other embodiments, the positional sensor system 608 can include other position sensors (e.g., accelerometers, rotary encoders, etc.) in addition to or in lieu of the shape sensor 733 and/or the position measuring device 739.

The shape sensor 733 of the positional sensor system 608 includes an optical fiber extending within and aligned with the elongate device 731. In one embodiment, the optical fiber of the shape sensor 733 has a diameter of approximately 200 µm. In other embodiments, the diameter of the optical fiber may be larger or smaller. The optical fiber of the shape sensor 733 forms a fiber optic bend sensor that is used to determine a shape, orientation, and/or pose of the elongate device 731. In some embodiments, optical fibers having Fiber Bragg Gratings (FBGs) can be used to provide strain measurements in structures in one or more dimensions. Various systems and methods for monitoring the shape and relative position of an optical fiber in three dimensions are described in further detail in U.S. Patent Application Publication No. 2006/0013523 (filed Jul. 13, 2005) (disclosing fiber optic position and shape sensing device and method relating thereto); U.S. Pat. No. 7,781,724 (filed on Sep. 26, 2006) (disclosing fiber-optic position and shape sensing device and method relating thereto); U.S. Pat. No. 7,772,541 (filed on Mar. 12, 2008) (disclosing fiber-optic position and/or shape sensing based on Rayleigh scatter); and U.S. Pat. No. 6,389,187 (filed on Jun. 17, 1998) (disclosing optical fiber bend sensors), which are all incorporated by reference herein in their entireties. In these and other embodiments, sensors of the present technology may employ other suitable strain sensing techniques, such as Rayleigh scattering, Raman scattering, Brillouin scattering, and Fluorescence scattering. In these and still other embodiments, the shape of the elongate device 731 may be determined using other techniques. For example, a history of the pose of the distal portion 738 of the elongate device 731 can be used to reconstruct the shape of elongate device 731 over an interval of time.

In some embodiments, the shape sensor 733 is fixed at a proximal point 734 on the instrument body 735 of the medical instrument system 604. In operation, for example, the shape sensor 733 measures a shape in the medical instrument reference frame ($X_M$, $Y_M$, $Z_M$) from the proximal point 734 to another point along the optical fiber, such as the distal portion 738 of the elongate device 731. The proximal point 734 of the shape sensor 733 may be movable along with instrument body 735 but the location of proximal point 734 may be known (e.g., via a tracking sensor (not shown) or other tracking device).

The position measuring device 739 of the positional sensor system 608 provides information about the position of the instrument body 735 as it moves along the insertion axis A on the insertion stage 728 of the manipulator assembly 602. In some embodiments, the position measuring device 739 includes resolvers, encoders, potentiometers, and/or other sensors that determine the rotation and/or orientation of actuators (not shown) controlling the motion of the instrument carriage 726 of the manipulator assembly 602 and, consequently, the motion of the instrument body 735 of the medical instrument system 604.

FIG. 8 is a schematic representation of a portion of the medical instrument system 604 of FIG. 7 extended within an anatomic region 850 (e.g., human lungs) of the patient 603 in accordance with various embodiments of the present technology. In particular, FIG. 8 illustrates the elongate device 731 of the medical instrument system 604 extending within branched anatomic passageways 852 of the anatomic region 850. The anatomic passageways 852 include a trachea 854 and a plurality of bronchial tubes 856.

As shown in FIG. 8, the elongate device 731 has a position, orientation, pose, and shape within the anatomic region 850, all or a portion of which (in addition to or in lieu of movement, such as speed or velocity) can be captured as positional sensor data by the positional sensor system 608 of FIGS. 6 and 7 (e.g., by the shape sensor 733 and/or the position measuring device 739 (FIG. 7)) to survey the anatomic passageways 852 of the anatomic region 850. In particular, the positional sensor system 608 can survey the anatomic passageways 852 by gathering positional sensor data of the medical instrument system 604 within the anatomic region 850 in the medical instrument frame of reference ($X_M$, $Y_M$, $Z_M$). The positional sensor data may at least in part be recorded as a set of two-dimensional or three-dimensional coordinate points. In the example of the anatomic region 850 being human lungs, the coordinate points may represent the locations of the distal portion 738 of the elongate device 731 and/or of other portions of the elongate device 731 while the elongate device 731 is advanced through the trachea 854 and the bronchial tubes 856. In these and other embodiments, the collection of coordinate points may represent the shape(s) of the elongate device 731 while the elongate device 731 is advanced through the anatomic region 850. In these and still other embodiments, the coordinate points may represent positional data of other portions (e.g., the medical instrument 732 (FIG. 7)) of the medical instrument system 604.

The coordinate points may together form a point cloud. For example, FIG. 9 illustrates a plurality of coordinate points 962 forming a point cloud 960 representing a shape of the elongate device 731 of FIG. 8 while the elongate device 731 is within the anatomic region 850 (FIG. 8) in accordance with various embodiments of the present technology. In particular, the point cloud 960 of FIG. 9 is generated from the union of all or a subset of the coordinate points 962 recorded by the positional sensor system 608 (FIG. 7) while the elongate device 731 is in the stationary position illustrated in FIG. 8.

In some embodiments, a point cloud (e.g., the point cloud 960) can include the union of all or a subset of coordinate points recorded by the positional sensor system 608 during an image capture period that spans multiple shapes, positions, orientations, and/or poses of the elongate device 731 within the anatomic region 850. In these embodiments, the point cloud can include coordinate points captured by the positional sensor system 608 that represent multiple shapes of the elongate device 731 while the elongate device 731 is advanced or moved through patient anatomy during the image capture period. Additionally, or alternatively, because the configuration, including shape and location, of the elongate device 731 within the patient 603 may change during the image capture period due to anatomical motion, the point cloud in some embodiments can comprise a plurality of coordinate points 962 captured by the positional sensor system 608 that represent the shapes of the elongate device 731 as the elongate device 731 passively moves within the patient 603. As described in greater detail below, a point cloud of coordinate points captured by the positional sensor system 608 can be registered to different models or datasets of patient anatomy.

Referring again to FIG. 7, the endoscopic imaging system 609 of the medical instrument system 604 includes one or more image capture devices 747 configured to capture one or more real navigational images of real patient anatomy (e.g., the anatomic passageways 852 of FIG. 8) while the elongate device 731 and/or the medical instrument 732 is within an anatomic region (e.g., the anatomic region 850 of FIG. 8) of the patient 603. For example, the endoscopic imaging system 609 can include an image capture device 747 positioned at the distal portion 737 of the medical instrument 732. In these and other embodiments, the endoscopic imaging system 609 can include one or more image capture devices (not shown) positioned at other locations along the medical instrument 732 and/or along the elongate device 731 (e.g., at the distal portion 738 of the elongate device 731).

In the embodiment illustrated in FIG. 8, the image capture device 747 of the medical instrument 732 (FIG. 7) is advanced to and positioned at the distal portion 738 of the elongate device 731. In this embodiment, the image capture device 747 can survey the anatomic passageways 852 by capturing real navigational images of the anatomic passageways 852 while the elongate device 731 is navigated through the trachea 854 and the bronchial tubes 856 of the anatomic region 850.

FIG. 10 is an example of a real navigational image 1070 (e.g., a still image, an image frame of a video, etc.) of patient anatomy of the anatomic region 850 of FIG. 8 (such as one of the anatomic passageways 852) captured via the image capture device 747 (FIG. 8). As shown, the real navigational image 1070 shows a branching point or carina 1071 of two anatomic passageways 852 within the anatomic region 850 from a viewpoint of the medical instrument 732 (FIG. 7). In this example, because the image capture device 747 is positioned at the distal portions 737 and 738 of the medical instrument 732 and the elongate device 731 (FIG. 8), respectively, the viewpoint of the real navigational image 1070 is from the distal portion 737 of the medical instrument 732 such that the medical instrument 732 and the elongate device 731 are not visible within the real navigational image 1070. In other embodiments, the image capture device 747 can be positioned at another location along the medical instrument 732 and/or along the elongate device 731 (FIGS. 7 and 8). In these embodiments, the endoscopic imaging system 109 (FIG. 7) can capture real navigational images from a corresponding viewpoint of the medical instrument 732 and/or of the elongate device 731. A portion of the medical instrument 732 and/or of the elongate device 731 may be visible within these real navigational images depending on the positions of the medical instrument 732 and the elongate device 731 relative to one another.

Referring again to FIG. 7, the real navigational images captured by the endoscopic imaging system 609 can facilitate navigation of the distal portion 738 of the elongate device 731 through patient anatomy (e.g., through the anatomic passageways 852 of FIG. 8) and/or delivery of the distal portion 738 of the elongate device 731 to a target location within the patient 603. In these and other embodiments, the real navigational images captured by the endoscopic imaging system 609 can facilitate (i) navigation of the distal portion 737 of the medical instrument 732 beyond the distal portion 738 of the elongate device 731, (ii) delivery of the distal portion 737 of the medical instrument 732 to a target location within the patient 603, and/or (iii) visualization of patient anatomy during a medical procedure. In some embodiments, each real navigational image captured by the endoscopic imaging system 609 can be associated with a time stamp and/or a position recorded in the medical instrument frame of reference ($X_M$, $Y_M$, $Z_M$). The real navigational images captured by the endoscopic imaging system 609 can optionally be used to improve a registration between a point cloud of coordinate points (e.g., the point cloud 960 of FIG. 9) generated by the positional sensor system 608 and image data captured by the imaging system 618.

As shown in FIG. 7, the imaging system 618 is arranged near the patient 603 to obtain three-dimensional images of the patient 603 (e.g., of the anatomic region 850 of FIG. 8). In some embodiments, the imaging system 618 includes one or more imaging technologies, including CT, MRI, fluoroscopy, thermography, ultrasound, OCT, thermal imaging, impedance imaging, laser imaging, nanotube X-ray imaging, and/or the like. The imaging system 618 is configured to generate image data of patient anatomy before, during, and/or after the elongate device 731 is extended within the patient 603. Thus, the imaging system 618 can be configured to capture preoperative, intraoperative, and/or postoperative three-dimensional images of patient anatomy. In these and other embodiments, the imaging system 618 may provide real-time or near real-time images of patient anatomy.

FIG. 11 illustrates an example of intraoperative image data 1180 of a portion 1155 of the anatomic region 850 of FIG. 8 captured during an image capture period by the imaging system 618 (FIG. 7) while the elongate device 731 of the medical instrument system 604 is extended within the anatomic region 850. As shown, the image data 1180 includes graphical elements 1181 representing the elongate device 731 and graphical elements 1182 representing the anatomic passageways 852 of the anatomic region 850.

All or a portion of the graphical elements 1181 and 1182 of the image data 1180 can be segmented and/or filtered to generate a virtual, three-dimensional model of the anatomic passageways 852 within the portion 1155 of the anatomic region 850 (with or without the medical instrument system 604). In some embodiments, the graphical elements 1181 and 1182 can additionally or alternatively be segmented and/or filtered to generate an image point cloud (not shown) of the medical instrument system 604 based, at least in part, on images captured by the imaging system 118 (FIG. 7) while the medical instrument system 604 is within the anatomic region 850. During the segmentation process, pixels or voxels generated from the image data 1180 may be partitioned into segments or elements or be tagged to indicate that they share certain characteristics or computed properties such as color, density, intensity, and texture. The segments or elements may then be converted to an anatomic model and/or to an image point cloud of the medical instrument system 604. Additionally, or alternatively, the segments or elements can be used to locate (e.g., calculate) and/or define a center line or other points running along the anatomic passageways 852. The generated anatomic model and/or the image point cloud may be two or three-dimensional and may be generated in an image reference frame ($X_I$, $Y_I$, $Z_I$).

As discussed above with respect to FIG. 6, the display system 610 (FIG. 6) of the medical system 600 (FIG. 6) can display various images or representations of patient anatomy and/or of the medical instrument system 604 based, at least in part, on data captured and/or generated by the positional sensor system 608, by the endoscopic imaging system 609, by the imaging system 618, and/or by the virtual visualization system 615. In various implementations, the images and/or representations can be utilized by the system to aid the operator 605 (FIG. 6) in conducting an image-guided medical procedure.

Figure 12:
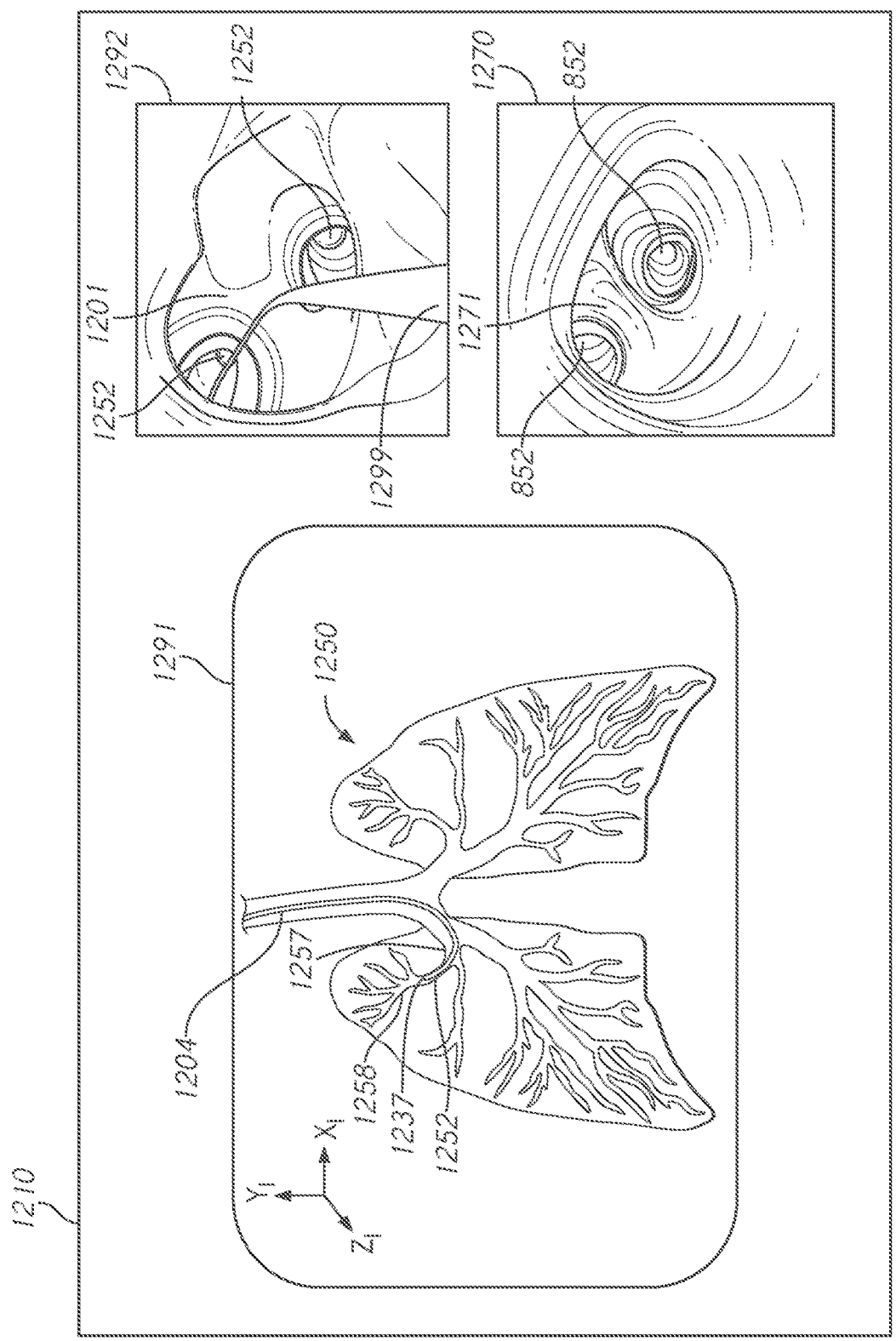
FIG. 12 is a schematic representation of a display of a display system displaying a composite virtual navigational image in which the medical instrument system of FIGS. 7 and 8 is registered to an anatomic model of the anatomic region of FIG. 8, a virtual navigational image of virtual patient anatomy, and a real navigational image of real patient anatomy within the anatomic region in accordance with various embodiments of the present technology.

FIG. 12 is a schematic representation of an example display 1210 produced by the display system 610 (FIG. 6) in accordance with various embodiments of the present technology. As shown, the display 1210 includes a real navigational image 1270, a composite virtual navigational image 1291 (also referred to as a "composite virtual image 1291"), and a virtual navigational image 1292. The real navigational image 1270 can be substantially the same as the real navigational image 1070 of FIG. 10. Thus, for example, the real navigational image 1270 can be captured by the endoscopic imaging system 609 (FIG. 7) and provided to the display system 610 (FIG. 6) to be presented on the display 1210 in real-time or near real-time. In the illustrated embodiment, the real navigational image 1270 illustrates real patient anatomy (e.g., a carina 1271 marking a branching point of two anatomic passageways 852) from a viewpoint oriented distally away from the distal portion 737 of the medical instrument 732 (FIG. 7).

The composite virtual image 1291 of FIG. 12 is displayed in the image reference frame ($X_I$, $Y_I$, $Z_I$) and includes an anatomic model 1250 generated from image data of the anatomic region 850 of FIG. 8 captured by the imaging system 618 (FIG. 7). The anatomic model 1250 is registered (i.e., dynamically referenced) with a point cloud of coordinate points (e.g., the point cloud 960 of FIG. 9) generated by the positional sensor system 608 (FIG. 7) to display a representation 1204 within the anatomic model 1250 of the tracked position, shape, pose, orientation, and/or movement of the medical instrument system 604 (e.g., of the elongate device 731 of FIG. 7) within the patient 603 (FIG. 7). In some embodiments, the composite virtual image 1291 is generated by the virtual visualization system 615 (FIG. 6) of the control system 612 (FIG. 6). Generating the composite virtual image 1291 involves registering the image reference frame ($X_I$, $Y_I$, $Z_I$) with the surgical reference frame ($X_S$, $Y_S$, $Z_S$) and/or to the medical instrument reference frame ($X_M$, $Y_M$, $Z_M$). This registration may rotate, translate, or otherwise manipulate by rigid and/or non-rigid transforms coordinate points of the point cloud (e.g., the coordinate points 962 of the point cloud 960 of FIG. 9) captured by the positional sensor system 608 to align the coordinate points with the anatomic model 1250. The registration between the image and surgical/instrument frames of reference may be achieved, for example, by using a point-based ICP technique, as described in U.S. Provisional Pat. App. Nos. 62/205,440 and No. 62/205,433, which are both incorporated by reference herein in their entireties. In other embodiments, the registration can be achieved using another point cloud registration technique.

Based, at least in part, on the registration, the virtual visualization system 615 can additionally or alternatively generate virtual navigational images (e.g., the virtual navigational image 1292 of FIG. 12) that include a virtual depiction of patient anatomy from a viewpoint of a virtual camera on the representation 1204 of the medical instrument system 604 (FIG. 8) within the anatomic model 1250. In the embodiment illustrated in FIG. 12, the virtual camera of the virtual navigational image 1292 is positioned at a distal portion 1237 of the representation 1204 such that (i) the virtual viewpoint of the virtual navigational image 1292 is directed distally away from the distal portion 1237 of the representation 1204 and (ii) the representation 1204 is not visible within the virtual navigational image 1292. In other embodiments, the virtual visualization system 615 can position the virtual camera (a) at another location along the representation 1204 and/or (b) in a different orientation such that the virtual navigational image 1292 has a corresponding virtual viewpoint. In some embodiments, depending on the position and orientation of the virtual camera and on the positions of the elongate device 731 and the medical instrument 732 relative to one another within the patient 603, the virtual visualization system 615 can render a virtual representation (not shown) of at least a portion of the elongate device 731 and/or of the medical instrument 732 into the virtual navigational image 1292.

In some embodiments, the virtual visualization system 615 can place the virtual camera within the anatomic model 1250 at a position and orientation corresponding to the position and orientation of the image capture device 747 within the patient 603 (FIG. 7). As further shown in FIG. 12, the virtual navigational image 1292 illustrates virtual patient anatomy, such as a carina 1201 marking a branching point of two anatomic passageways 1252 of the anatomic model 1250, from substantially the same location at which the real navigational image 1270 is captured by the image capture device 747 (FIG. 7). Thus, the virtual navigational image 1292 provides a rendered estimation of patient anatomy visible to the image capture device 747 at a given location within the anatomic region 850 of FIG. 8. Because the virtual navigational image 1292 is based, at least in part, on the registration of a point cloud generated by the positional sensor system 608 and image data captured by the imaging system 618, the correspondence between the virtual navigational image 1292 and the real navigational image 1270 provides insight regarding the accuracy of the registration and can be used to improve the registration. Furthermore, the real navigational images (e.g., the real navigational image 1270) captured by the endoscopic imaging system 609 (FIG. 7) can (a) provide information regarding the position and orientation of the medical instrument system 604 (FIG. 6) within the patient 603, (b) provide information regarding portions of an anatomic region actually visited by the medical instrument system, and/or (c) help identify patient anatomy (e.g., branching points of anatomic passageways) proximate the medical instrument system 604, any one or more of which can be used to improve the accuracy of the registration.

As further shown in FIG. 12, the virtual navigational image 1292 can optionally include a navigation path overlay 1299. In some embodiments, the navigation path overlay 1299 is used to aid an operator 605 (FIG. 6) to navigate the medical instrument system 604 (FIG. 6) through anatomic passageways of an anatomic region to a target location within a patient 603. For example, the navigation path overlay 1299 can illustrate a "best" path through an anatomic region for an operator 605 to follow to deliver the distal portions 737 and/or 738 of the medical instrument 732 and/or of the elongate device 731, respectively, to a target location within the patient 603. In some embodiments, the navigation path overlay 1299 can be aligned with a centerline of or another line along (e.g., the floor of) a corresponding anatomic passageway.

C. EXAMPLES

Several aspects of the present technology are set forth in the following examples. Although several aspects of the present technology are set forth in examples directed to systems, computer-readable mediums, and methods, any of these aspects of the present technology can similarly be set forth in examples directed to any of systems, computer-readable mediums, and methods in other embodiments.

1. A system for planning a medical procedure, the system comprising:
 a processor; and
 a memory operably coupled to the processor and storing instructions that, when executed by the processor, cause the system to perform operations comprising—
   receiving a three-dimensional model of an anatomic region of a patient, and evaluating whether the three-dimensional model is suitable for use in a registration procedure to be performed in the anatomic region, wherein the evaluating comprises—
     analyzing a span of the three-dimensional model along at least two different directions,
     determining whether the three-dimensional model includes at least one segmented component corresponding to at least one structure of the anatomic region, and
   performing a registration between the three-dimensional model and a virtual registration data set.

2. The system of claim 1 wherein the at least two different directions comprise a first direction and a second direction, and wherein the operations further comprise:
 calculating a first span value of the three-dimensional model along the first direction;
 calculating a second span value of the three-dimensional model along the second direction; and
 determining whether one or more of the first or second span values exceed a threshold value.

3. The system of example 1 or example 2 wherein the at least one structure includes one or more of the following: a trachea, a main carina, a left main bronchus, a right main bronchus, and a sub-segmental bronchus.

4. The system of example 1 or example 2 wherein the operations further comprise determining whether the at least one segmented component has a length greater than or equal to a minimum length.

5. The system of example 1 or example 2 wherein the at least one structure is a branched structure having a plurality of generations, and wherein the operations further comprise determining whether the at least one segmented component covers a minimum number of the generations of the branched structure.

6. The system of any one of examples 1-5 wherein the virtual registration data set includes a plurality of data points along or near a survey trajectory within the three-dimensional model.

7. The system of any one of examples 1-6 wherein the operations further comprise performing a plurality of registrations between the three-dimensional model and the virtual registration data set, wherein each registration is performed using a different initial seed.

8. The system of example 7 wherein the operations further comprise determining an amount of variance between the registrations.

9. The system of any one of examples 1-6 wherein the operations further comprise performing a plurality of registrations, and wherein each of the registrations is performed between the three-dimensional model and a different virtual registration data set.

10. The system of example 9 wherein the operations further comprise determining an accuracy of each registration.

11. The system of example 10 wherein the accuracy of each registration is evaluated at one or more portions of the three-dimensional model corresponding to one or more target sites in the anatomic region.

12. The system of any one of examples 1-11 wherein the operations further comprise outputting feedback indicative of whether the three-dimensional model is suitable for use in the registration procedure.

13. A non-transitory, computer-readable medium storing instructions thereon that, when executed by one or more processors of a computing system, cause the computing system to perform operations comprising:
receiving a three-dimensional model of an anatomic region of a patient; and
evaluating whether the three-dimensional model is suitable for use in a registration procedure to be performed in the anatomic region, wherein the evaluating comprises—
analyzing a span of the three-dimensional model along at least two different directions,
determining whether the three-dimensional model includes at least one segmented component corresponding to at least one structure of the anatomic region, and
performing a registration between the three-dimensional model and a virtual registration data set.

14. The non-transitory, computer-readable medium of example 13 wherein the at least two different directions comprise a first direction and a second direction, and wherein the operations further comprise calculating a first eigenvalue and a second eigenvalue, the first eigenvalue corresponding to a first span of the three-dimensional model along the first direction and the second eigenvalue corresponding to a second span of the three-dimensional model along the second direction.

15. The non-transitory, computer-readable medium of example 13 or example 14 wherein the at least one structure includes one or more of the following: a trachea, a main carina, a left main bronchus, a right main bronchus, and a sub-segmental bronchus.

16. The non-transitory, computer-readable medium of example 13 or example 14 wherein the operations further comprise determining whether the at least one segmented component has a length greater than or equal to a minimum length.

17. The non-transitory, computer-readable medium of example 13 or example 14 wherein the at least one structure is a branched structure having a plurality of generations and the operations further comprise determining whether the at least one segmented component covers a minimum number of the generations of the branched structure.

18. The non-transitory, computer-readable medium of any one of examples 13-17 wherein the operations further comprise generating the virtual registration data set by:
selecting a subset of passageways of the three-dimensional model;
creating a representation of a centerline of the subset of the passageways; and
adding randomized noise to the representation.

19. The non-transitory, computer-readable medium of any one of examples 13-18 wherein the operations further comprise performing a plurality of registrations between the three-dimensional model and the virtual registration data set, wherein each registration is performed using a randomized initial seed.

20. The non-transitory, computer-readable medium of example 19 wherein the operations further comprise determining an amount of variance between the registrations.

21. The non-transitory, computer-readable medium of any one of examples 13-18 wherein the operations further comprise performing a plurality of registrations, wherein each of the registrations is performed between the three-dimensional model and a different virtual registration data set.

22. The non-transitory, computer-readable medium of example 21 wherein the operations further comprise determining an accuracy of each registration.

23. The non-transitory, computer-readable medium of example 22 wherein the accuracy of each registration is evaluated at or near a location of a target lesion for a biopsy procedure.

24. The non-transitory, computer-readable medium of any one of examples 13-23 wherein the operations further comprise outputting feedback indicative of whether the three-dimensional model is suitable for use in the registration procedure.

25. A method, comprising:
receiving a three-dimensional model of an anatomic region of a patient; and evaluating whether the three-dimensional model is suitable for use in a registration procedure to be performed in the anatomic region, wherein the evaluating comprises—
analyzing a span of the three-dimensional model along at least two different directions,
determining whether the three-dimensional model includes at least one segmented component corresponding to at least one structure of the anatomic region, and
performing a registration between the three-dimensional model and a virtual registration data set.

26. A system for planning a medical procedure, the system comprising:
a processor; and a memory operably coupled to the processor and storing instructions that, when executed by the processor, cause the system to perform operations comprising:
receiving a three-dimensional model of an anatomic region of a patient;
generating a survey trajectory through a portion of the three-dimensional model;
generating a virtual registration data set including a plurality of data points along or near the survey trajectory;
performing a plurality of registrations between the three-dimensional model and the virtual registration data set; and
evaluating, based on the plurality of registrations, whether the survey trajectory is suitable for use in a registration procedure to be performed in the anatomic region.

27. The system of example 26 wherein the survey trajectory is generated by selecting one or more passageways within the three-dimensional model, wherein the passageways are selected based on one or more of depth, accessibility, and distinctiveness.

28. The system of example 26 wherein the survey trajectory is generated based on a location of a target site within the anatomic region.

29. The system of any one of examples 26-28 wherein the virtual registration data set is configured to simulate positional data generated by a medical device traveling along the survey trajectory.

30. The system of any one of examples 26-29 wherein each registration is performed using a different initial seed.

31. The system of any one of examples 26-30 wherein the operations further comprise determining an amount of variance between the registrations.

32. The system of example 31 wherein the survey trajectory is suitable for use in the registration procedure if the amount of variance is less than or equal to a threshold value.

33. The system of example 26 wherein the operations further comprise:
determining a plurality of survey trajectories through the portion of the three-dimensional model; and
for each of the survey trajectories—
generating a respective virtual registration data set including a respective plurality of data points along or near the survey trajectory, and
performing a respective plurality of registrations between the three-dimensional model and the respective virtual registration data set.

34. The system of example 33 wherein the operations further comprise selecting a subset of the survey trajectories for use in the registration procedure.

35. The system of any one of examples 26-32 wherein the operations further comprise outputting a graphical representation of the survey trajectory, wherein the graphical representation is configured to be displayed to an operator during the registration procedure.

36. A non-transitory, computer-readable medium storing instructions thereon that, when executed by one or more processors of a computing system, cause the computing system to perform operations comprising:
receiving a three-dimensional model of an anatomic region of a patient;
generating a survey trajectory through a portion of the three-dimensional model;
generating a virtual registration data set including a plurality of data points along or near the survey trajectory;
performing a plurality of registrations between the three-dimensional model and the virtual registration data set; and
evaluating, based on the plurality of registrations, whether the survey trajectory is suitable for use in a registration procedure to be performed in the anatomic region.

37. The non-transitory, computer-readable medium of example 36 wherein the survey trajectory is generated by selecting one or more passageways within the three-dimensional model.

38. The non-transitory, computer-readable medium of example 37 wherein the one or more passageways are selected, at least partly, based on input from an operator.

39. The non-transitory, computer-readable medium of any one of examples 36-38 wherein the virtual registration data set is configured to simulate survey data generated by a medical device traveling along the survey trajectory.

40. The non-transitory, computer-readable medium of any one of examples 36-39 wherein each registration is performed using a randomized initial seed.

41. The non-transitory, computer-readable medium of any one of examples 36-40 wherein the operations further comprise determining an amount of variance between the registrations.

42. The non-transitory, computer-readable medium of example 41 wherein the survey trajectory is suitable for use in the registration procedure if the amount of variance is less than or equal to a threshold value.

43. The non-transitory, computer-readable medium of example 36 wherein the operations further comprise:
determining a plurality of survey trajectories through the portion of the three-dimensional model; and
for each of the survey trajectories—
generating a respective virtual registration data set including a respective plurality of data points along or near the survey trajectory, and
performing a respective plurality of registrations between the three-dimensional model and the respective virtual registration data set.

44. The non-transitory, computer-readable medium of example 43 wherein the operations further comprise selecting a subset of the survey trajectories for use in the registration procedure.

45. The non-transitory, computer-readable medium of any one of examples 36-42 wherein the operations further comprise outputting a graphical representation of the subset of the survey trajectories, wherein the graphical representation is configured to be displayed to an operator during the registration procedure.

46. A method, comprising:
receiving a three-dimensional model of an anatomic region of a patient;
generating a survey trajectory through a portion of the three-dimensional model;
generating a virtual registration data set including a plurality of data points along or near the survey trajectory;
performing a plurality of registrations between the three-dimensional model and the virtual registration data set; and evaluating, based on the plurality of registrations, whether the survey trajectory is suitable for use in a registration procedure to be performed in the anatomic region.

D. CONCLUSION

The systems and methods described herein can be provided in the form of tangible and non-transitory machinereadable medium or media (such as a hard disk drive, hardware memory, etc.) having instructions recorded thereon for execution by a processor or computer. The set of instructions can include various commands that instruct the computer or processor to perform specific operations such as the methods and processes of the various embodiments described here. The set of instructions can be in the form of a software program or application. The computer storage media can include volatile and non-volatile media, and removable and non-removable media, for storage of information such as computer-readable instructions, data structures, program modules or other data. The computer storage media can include, but are not limited to, RAM, ROM, EPROM, EEPROM, flash memory or other solid-state memory technology, CD-ROM, DVD, or other optical storage, magnetic disk storage, or any other hardware medium which can be used to store desired information and that can be accessed by components of the system. Components of the system can communicate with each other via wired or wireless communication. The components can be separate from each other, or various combinations of components can be integrated together into a monitor or processor or contained within a workstation with standard computer hardware (for example, processors, circuitry, logic circuits, memory, and the like). The system can include processing devices such as microprocessors, microcontrollers, integrated circuits, control units, storage media, and other hardware.

Although many of the embodiments are described above in the context of navigating and performing medical procedures within lungs of a patient, other applications and other embodiments in addition to those described herein are within the scope of the present technology. For example, unless otherwise specified or made clear from context, the devices, systems, methods, and computer program products of the present technology can be used for various image-guided medical procedures, such as medical procedures performed on, in, or adjacent hollow patient anatomy, and, more specifically, in procedures for surveying, biopsying, ablating, or otherwise treating tissue within and/or proximal the hollow patient anatomy. Thus, for example, the systems, devices, methods, and computer program products of the present disclosure can be used in one or more medical procedures associated with other patient anatomy, such as the bladder, urinary tract, GI system, and/or heart of a patient.

As used herein, the term "operator" shall be understood to include any type of personnel who may be performing or assisting a medical procedure and, thus, is inclusive of a physician, a surgeon, a doctor, a nurse, a medical technician, other personnel or user of the technology disclosed herein, and any combination thereof. Additionally, or alternatively, the term "patient" should be considered to include human and/or non-human (e.g., animal) patients upon which a medical procedure is being performed.

From the foregoing, it will be appreciated that specific embodiments of the technology have been described herein for purposes of illustration, but well-known structures and functions have not been shown or described in detail to avoid unnecessarily obscuring the description of the embodiments of the technology. To the extent any materials incorporated herein by reference conflict with the present disclosure, the present disclosure controls. Where the context permits, singular or plural terms can also include the plural or singular term, respectively. Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. As used herein, the phrase "and/or" as in "A and/or B" refers to A alone, B alone, and both A and B. Where the context permits, singular or plural terms can also include the plural or singular term, respectively. Additionally, the terms "comprising," "including," "having" and "with" are used throughout to mean including at least the recited feature(s) such that any greater number of the same feature and/or additional types of other features are not precluded.

Furthermore, as used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result.

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments can perform steps in a different order. As another example, various components of the technology can be further divided into subcomponents, and/or various components and/or functions of the technology can be combined and/or integrated. Furthermore, although advantages associated with certain embodiments of the technology have been described in the context of those embodiments, other embodiments can also exhibit such advantages, and not all embodiments need necessarily exhibit such advantages to fall within the scope of the technology.

It should also be noted that other embodiments in addition to those disclosed herein are within the scope of the present technology. For example, embodiments of the present technology can have different configurations, components, and/or procedures in addition to those shown or described herein. Moreover, a person of ordinary skill in the art will understand that these and other embodiments can be without several of the configurations, components, and/or procedures shown or described herein without deviating from the present technology. Accordingly, the disclosure and associated technology can encompass other embodiments not expressly shown or described herein.

What is claimed is:

1. A system for planning a medical procedure, the system comprising:
 a processor; and
 a memory operably coupled to the processor and storing instructions that, when executed by the processor, cause the system to perform operations comprising:
  receiving a three-dimensional model of an anatomic region of a patient, and evaluating whether the three-dimensional model is suitable for use in a registration procedure to be performed in the anatomic region, wherein the evaluating comprises—
  analyzing a span of the three-dimensional model along at least two different directions,
  determining whether the three-dimensional model includes at least one segmented component corresponding to at least one structure of the anatomic region, and
  performing a registration between the three-dimensional model and a virtual registration data set.

2. The system of claim 1 wherein the at least two different directions comprise a first direction and a second direction, and wherein the operations further comprise:
  calculating a first span value of the three-dimensional model along the first direction;
  calculating a second span value of the three-dimensional model along the second direction; and
  determining whether one or more of the first or second span values exceed a threshold value.

3. The system of claim 1 wherein the at least one structure includes one or more of the following: a trachea, a main carina, a left main bronchus, a right main bronchus, and a sub-segmental bronchus.

4. The system of claim 1 wherein the operations further comprise determining whether the at least one segmented component has a length greater than or equal to a minimum length.

5. The system of claim 1 wherein the at least one structure is a branched structure having a plurality of generations, and wherein the operations further comprise determining whether the at least one segmented component covers a minimum number of the generations of the branched structure.

6. The system of claim 1 wherein the virtual registration data set includes a plurality of data points along or near a survey trajectory within the three-dimensional model.

7. The system of claim 1 wherein the operations further comprise performing a plurality of registrations between the three-dimensional model and the virtual registration data set, wherein each registration is performed using a different initial seed.

8. The system of claim 7 wherein the operations further comprise determining an amount of variance between the registrations.

9. The system of claim 1 wherein the operations further comprise performing a plurality of registrations, and wherein each of the registrations is performed between the three-dimensional model and a different virtual registration data set.

10. The system of claim 9 wherein the operations further comprise determining an accuracy of each registration.

11. The system of claim 10 wherein the accuracy of each registration is evaluated at one or more portions of the three-dimensional model corresponding to one or more target sites in the anatomic region.

12. The system of claim 1 wherein the operations further comprise outputting feedback indicative of whether the three-dimensional model is suitable for use in the registration procedure.

13. A system for planning a medical procedure, the system comprising:
  a processor; and
  a memory operably coupled to the processor and storing instructions that, when executed by the processor, cause the system to perform operations comprising:
    receiving a three-dimensional model of an anatomic region of a patient;
    generating a survey trajectory through a portion of the three-dimensional model;
    generating a virtual registration data set including a plurality of data points along or near the survey trajectory;
    performing a plurality of registrations between the three-dimensional model and the virtual registration data set; and
    evaluating, based on the plurality of registrations, whether the survey trajectory is suitable for use in a registration procedure to be performed in the anatomic region.

14. The system of claim 13 wherein the survey trajectory is generated by selecting one or more passageways within the three-dimensional model, wherein the passageways are selected based on one or more of depth, accessibility, and distinctiveness.

15. The system of claim 13 wherein the survey trajectory is generated based on a location of a target site within the anatomic region.

16. The system of claim 13 wherein the virtual registration data set is configured to simulate positional data generated by a medical device traveling along the survey trajectory.

17. The system of claim 13 wherein each registration is performed using a different initial seed.

18. The system of claim 13 wherein the operations further comprise determining an amount of variance between the registrations.

19. The system of claim 18 wherein the survey trajectory is suitable for use in the registration procedure if the amount of variance is less than or equal to a threshold value.

20. The system of claim 13 wherein the operations further comprise:
  determining a plurality of survey trajectories through the portion of the three-dimensional model; and
  for each of the survey trajectories—
  generating a respective virtual registration data set including a respective plurality of data points along or near the survey trajectory, and
  performing a respective plurality of registrations between the three-dimensional model and the respective virtual registration data set.

* * * * *